(12) United States Patent
Takahashi et al.

(10) Patent No.: US 7,842,818 B2
(45) Date of Patent: Nov. 30, 2010

(54) PROCESS FOR PREPARATION OF TETRASUBSTITUTED 5-AZASPIRO[2.4]-HEPTANE DERIVATIVES AND OPTICALLY ACTIVE INTERMEDIATES THEREOF

(75) Inventors: Hisashi Takahashi, Edogawa-ku (JP); Rie Miyauchi, Edogawa-ku (JP); Yasuyuki Takeda, Edogawa-ku (JP); Kazuo Kanai, Edogawa-ku (JP); Junichi Kuroyanagi, Edogawa-ku (JP); Satoshi Komoriya, Edogawa-ku (JP); Makoto Takemura, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 334 days.

(21) Appl. No.: 12/067,737

(22) PCT Filed: Sep. 28, 2006

(86) PCT No.: PCT/JP2006/319251
§ 371 (c)(1),
(2), (4) Date: Mar. 21, 2008

(87) PCT Pub. No.: WO2007/037303
PCT Pub. Date: Apr. 5, 2007

(65) Prior Publication Data
US 2009/0270637 A1    Oct. 29, 2009

(30) Foreign Application Priority Data
Sep. 28, 2005    (JP)    .............................. 2005-282973

(51) Int. Cl.
*C07D 209/54* (2006.01)
(52) U.S. Cl. ..................................................... 548/408
(58) Field of Classification Search ................... 548/408
See application file for complete search history.

(56) References Cited

U.S. PATENT DOCUMENTS 7,563,805 B2 *    7/2009    Takahashi et al. ........... 514/312

FOREIGN PATENT DOCUMENTS

| JP | 3 95176 | 4/1991 |
| JP | 4 74167 | 3/1992 |
| JP | 5 262738 | 10/1993 |
| JP | 7 309864 | 11/1995 |
| JP | 9 208561 | 8/1997 |
| WO | WO 2006/123792 | 11/2006 |

OTHER PUBLICATIONS

Ezquerra et al. (Tetrahedron Assymetry, 1994, vol. 5 (5); p. 921-926.).*
Brackmann and de Meijere (Chemical Reviews, 2007, vol. 107 (11); p. 4538-4583).*

Suto, Mark et al., "Synthesis of Chiral 3-Substituted-3-Aminomethylpyrrolidines and Related Compounds", Journal of Heterocyclic Chemistry, vol. 29, No. 6, pp. 1441 to 1448, 1992.
Sole, Daniel et al., "Palladium-Catalyzed Intramolecular Coupling of Amino-Tethered Vinyl Halides With Ketones, Esters, and Nitriles Using Potassium Phenoxide as the Base", Advanced Synthesis & Catalysis, vol. 346, No. 13-15, pp. 1646 to 1650, 2004.
Tarnchompoo, Bonkoch et al., "Pyrrolidine and α-Methylene-Y-Lactam From the Cyclization of α-(Alkylaminoethyl) Acrylate: Synthesis of Aza-Sarkomycins", Tetrahedron Letters, vol. 28, No. 52, pp. 6675 to 6678, 1987.

* cited by examiner

Primary Examiner—Kamal A Saeed
Assistant Examiner—Valerie Rodriguez-Garcia
(74) Attorney, Agent, or Firm—Oblon, Spivak, McClelland, Maier & Neustadt, L.L.P.

(57) ABSTRACT

The present invention provides a method for effectively producing an optically active form of tetrasubstituted-5-azaspiro [2.4]heptane derivative, which serves as a useful production intermediate for quinolonecarboxylic acid antibacterial agents, and intermediates for the derivative. The present invention is directed to a method for producing a compound (VII) according to the following scheme.

-continued
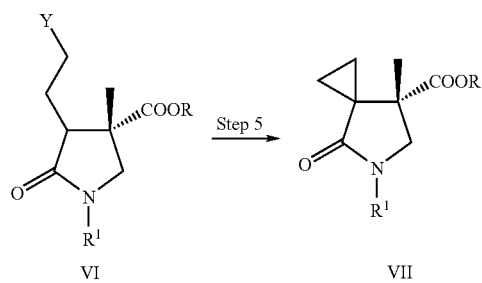
14 Claims, 1 Drawing Sheet

PROCESS FOR PREPARATION OF TETRASUBSTITUTED 5-AZASPIRO[2.4]-HEPTANE DERIVATIVES AND OPTICALLY ACTIVE INTERMEDIATES THEREOF

TECHNICAL FIELD

The present invention relates to a method for effectively producing an optically active form of tetrasubstituted-5-azaspiro[2.4]heptane derivative, which serves as a useful production intermediate for quinolonecarboxylic acid antibacterial agents, and to optically active intermediates for the derivative.

BACKGROUND ART

A 7-amino-7-methyl-5-azaspiro[2.4]heptan-5-yl group is a suitable 7-position substituent for a quinolonecarboxylic acid antibacterial agent (corresponds to 10-position in case of pyridobenzoxazinecarboxylic acid derivative), and a quinolone compound having this substituent is a suitable antibacterial agent exhibiting excellent antibacterial activity, suitable pharmacokinetics, and high safety (Patent Document 1). The 7-amino-7-methyl-5-azaspiro[2.4]heptan-5-yl group has a chiral amino-substituted 7-position, which by itself generates a pair of optical isomers of a quinolone compound. It has been previously revealed that one of the isomers exhibits more potent antibacterial activity and further expresses other physiological activities compared to the other isomer (Patent Document 1).

A quinolone compound having the above substituent is readily produced from a 7-amino-7-methyl-5-azaspiro[2.4]heptane compound, and in an easier manner, by use of one optically active form of said compound. One exemplary method for producing the compound is represented by the following scheme (Patent Document 1):

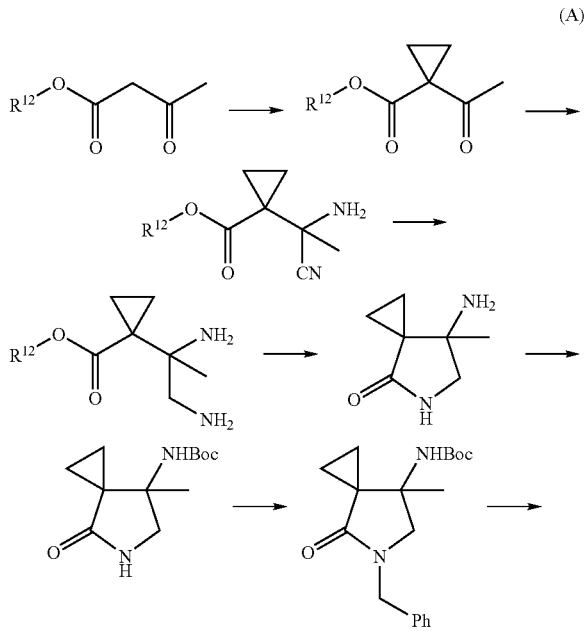

(A)

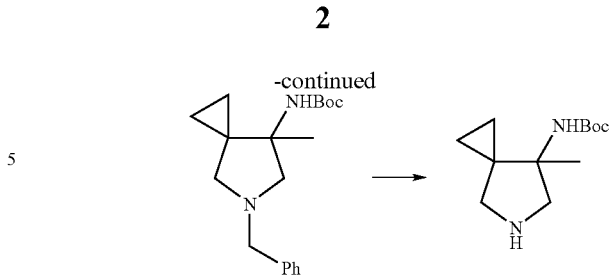

(wherein Boc represents a tert-butoxycarbonyl group and $R^{12}$ represents a C1 to C6 alkyl group).

Specifically, the previous method for producing the aforementioned compound (A) is characterized by the following steps: producing an amino-cyano compound from an acetoacetate ester compound through Strecker reaction at ketone moiety thereof; transforming a cyano group of the amino-cyano compound to an aminomethyl group; and then subjecting the aminomethyl group to intramolecular cyclization with an ester moiety (carboxyl unit) to form a pyrrolidone derivative.

Patent Document 1: Japanese Patent Application No. 2005

DISCLOSURE OF THE INVENTION

Problems to be Solved by the Invention

However, in the aforementioned method, when the amino-cyano compound having a non-protected amino group is used, retro-Strecker reaction may occur during reduction of the cyano group to the aminomethyl group in the presence of a metallic catalyst such as Raney nickel. Such a reaction causes problems such as a decreased yield of a target product or formation of a complex reaction mixture, as well as requiring purification. Therefore, the above method is to be further improved for serving as an industrial application.

Conventionally, an optically active 7-amino-7-methyl-5-azaspiro[2.4]heptane for constructing an optically active 7-amino-7-methyl-5-azaspiro[2.4]heptan-5-yl group is obtained through optical resolution of an appropriate intermediate by means of HPLC using a chiral column. However, the conventional method has drawbacks since the HPLC optical resolution is not suitable for industrial application due to its low processing capacity and does not allow to reuse non-target isomers. Thus, the conventional method is unsatisfactory as a method for producing an optically active compound.

It has been indicated that a quinolone compound having an optically active 7-amino-7-methyl-5-azaspiro[2.4]heptan-5-yl group provides one optical isomer exhibiting more excellent physiological activities than those of the other optical isomer (Patent Document 1). However, stereo-configuration of the 7-amino group in this substituent has not been elucidated in detail, and thus it has not been determined which isomer (i.e., (7R)-form or (7S)-form) exhibits more excellent activities.

In view of the forgoing, an object of the present invention is to provide a method for effectively producing an optically active (7S)-7-amino-7-methyl-5-azaspiro[2.4]heptane derivative having a specific stereo-configuration (7S). The derivative is useful for constructing a 7-position substituent for a quinolonecarboxylic acid antibacterial agent (corresponds to 10-position in case of pyridobenzoxazinecarboxylic acid derivative) to provide a quinolone compound exhibiting an excellent physiological activity. Another object of the invention is to provide intermediate compounds useful for the production of the derivative.

MEANS FOR SOLVING THE PROBLEMS

The present inventors have conducted extensive studies, and have found that, by use of a (3S)-3-methyl-5-oxo-1-[(1R)-1-phenylethyl]pyrrolidine-3-carboxylate ester compound as a chiral building block and a starting material, a (7S)-7-methyl-4-oxo-5-[(1R)-phenylethyl]-5-azaspiro[2.4]heptane-7-carboxylate ester compound can be effectively produced in a simple manner.

Since the (7S)-7-methyl-4-oxo-5-[(1R)-phenylethyl]-5-azaspiro[2.4]heptane-7-carboxylate ester compound has high crystallinity, a 7S configuration of the 7-position amino group has been readily determined through X-ray crystallographic structural analysis. Based on the determined stereo-configuration of the compound, stereo-configuration of a series of compounds prepared via the compound has also been elucidated.

The present inventors have also found that a spirocyclic structure can be constructed in a simple manner by exo-methylenating a (3S)-3-methyl-5-oxo-1-[(1R)-1-phenylethyl]pyrrolidine-3-carboxylate ester compound and subjecting the methylene group to cycloaddition reaction.

The inventors have also found a method for producing a (7S)-7-amino-7-methyl-5-azaspiro[2.4]heptane derivative from a (7S)-7-methyl-4-oxo-5-[(1R)-phenylethyl]-5-azaspiro[2.4]heptane-7-carboxylate ester derivative (VII), which has been produced in the aforementioned production steps.

Accordingly, the present invention is directed to a method for producing a compound represented by formula (VII):

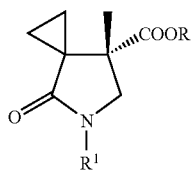

(VII)

(wherein R represents an aryl group which may have a substituent, an aralkyl group which may have a substituent, a C1 to C6 alkyl group which may have a substituent, or a chiral auxiliary which can form an ester bond with carboxylic acid; and R¹ represents an aralkyl group which may have a substituent), which comprises:

reacting a compound represented by formula (I):

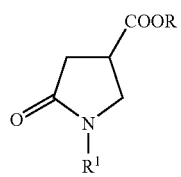

(I)

(wherein R and R¹ have the same meanings as defined above) with a methylating reagent in the presence of a base to produce a compound represented by formula (II):

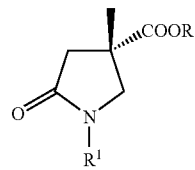

(II)

(wherein R¹ and R have the same meanings as defined above);

reacting the compound represented by formula (II) with a compound represented by formula (III):

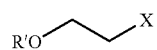

(III)

(wherein R' represents a protective group for hydroxy group, and X represents a halogen atom or a leaving group employed in nucleophilic substitution) in the presence of a base to produce a compound represented by formula (IV):

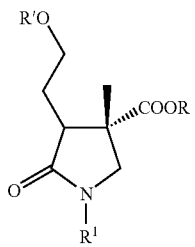

(IV)

(wherein R¹, R, and R' have the same meanings as defined above);

removing the protective group from the compound represented by formula (IV) to produce a compound represented by formula (V)

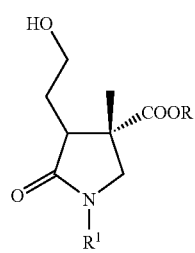

(V)

(wherein R¹ and R have the same meanings as defined above)

transforming the hydroxy group of the compound represented by formula (V) to a halogen atom or a leaving group employed in nucleophilic substitution to form a compound represented by formula (VI):

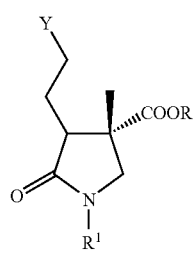

(VI)

(wherein Y represents a halogen atom or a leaving group employed in nucleophilic substitution, and R¹ and R have the same meanings as defined above); and treating the compound represented by formula (VI) under basic conditions.

The present invention is also directed to a method for producing a compound represented by formula (VII):

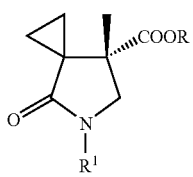

(VII)

(wherein R¹ and R have the same meanings as defined above), which comprises:

exo-methylenating the compound represented by formula (II) to produce a compound represented by formula (VIII):

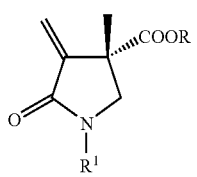

(VIII)

(wherein R¹ and R have the same meanings as defined above); and subjecting the exo-methylene group of the compound represented by formula (VIII) to a cyclopropanation.

The present invention is also directed to a method for producing a compound represented by formula (XII):

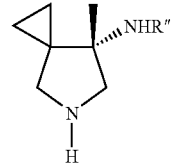

(XII)

(wherein R" represents a hydrogen atom or a protective group for amino group), which comprises:

treating a compound represented by formula (VII):

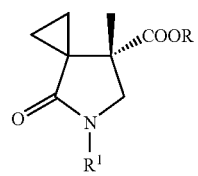

(VII)

(wherein R¹ and R have the same meanings as defined above) under ester hydrolysis conditions to produce a compound represented by formula (IX):

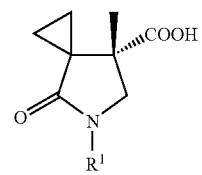

(IX)

(wherein R¹ has the same meaning as defined above);

subjecting the carboxy group of the compound represented by formula (IX) to rearrangement so as to transform to an amino group, to thereby produce a compound represented by formula (X):

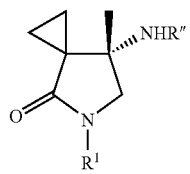

(X)

(wherein R" and R¹ have the same meanings as defined above);

treating the compound represented by formula (X), directly or after transformation of the carbonyl group to a thiocarbonyl group, under reducing conditions to produce a compound represented by formula (XI):

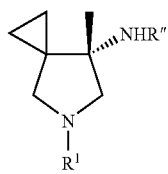

(wherein R¹ and R" have the same meanings as defined above) and subjecting the substituent R¹ of the compound represented by formula (XI) to deprotection reaction.

The present invention is also directed to the following compounds.

A compound represented by formula (II):

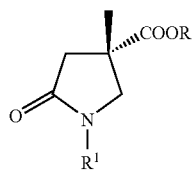

(wherein R represents an aryl group which may have a substituent, an aralkyl group which may have a substituent, a C1 to C6 alkyl group which may have a substituent, or a chiral auxiliary which can form an ester bond with carboxylic acid; and R' represents an aralkyl group which may have a substituent).

A compound represented by formula (IV):

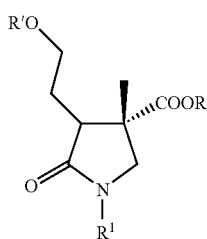

(wherein R represents an aryl group which may have a substituent, an aralkyl group which may have a substituent, a C1 to C6 alkyl group which may have a substituent, or a chiral auxiliary which can form an ester bond with carboxylic acid; R' represents an aralkyl group which may have a substituent; and R' represents a protective group for hydroxy group).

A compound represented by formula (V):

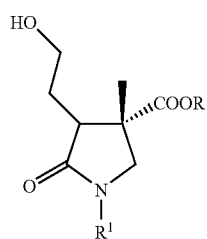

(wherein R represents an aryl group which may have a substituent, an aralkyl group which may have a substituent, a C1 to C6 alkyl group which may have a substituent, or a chiral auxiliary which can form an ester bond with carboxylic acid; and R¹ represents an aralkyl group which may have a substituent).

A compound represented by formula (VI):

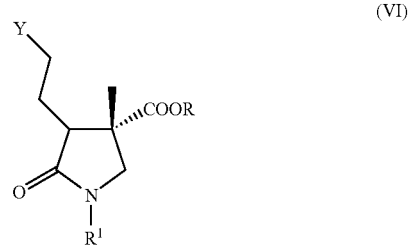

(wherein Y represents a halogen atom or a leaving group employed in nucleophilic substitution; R represents an aryl group which may have a substituent, an aralkyl group which may have a substituent, a C1 to C6 alkyl group which may have a substituent, or a chiral auxiliary which can form an ester bond with carboxylic acid; and R¹ represents an aralkyl group which may have a substituent).

A compound represented by formula (VII):

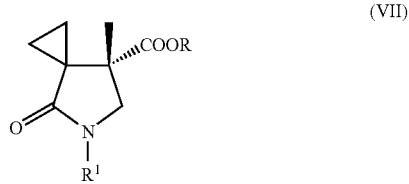

(wherein R represents an aryl group which may have a substituent, an aralkyl group which may have a substituent, a C1 to C6 alkyl group which may have a substituent, or a chiral auxiliary which can form an ester bond with carboxylic acid; and R¹ represents an aralkyl group which may have a substituent).

A compound represented by formula (VIII):

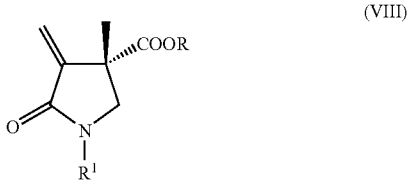

(wherein R represents an aryl group which may have a substituent, an aralkyl group which may have a substituent, a C1 to C6 alkyl group which may have a substituent, or a chiral auxiliary which can form an ester bond with carboxylic acid; and R¹ represents an aralkyl group which may have a substituent).

A compound represented by formula (IX):

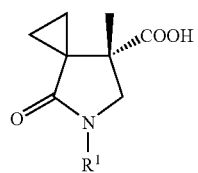

(IX)

(wherein R¹ represents an aralkyl group which may have a substituent).

A compound represented by formula (X):

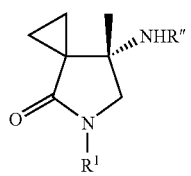

(X)

(wherein R" represents a hydrogen atom or a protective group for amino group, and R¹ represents an aralkyl group which may have a substituent).

A compound represented by formula (XI):

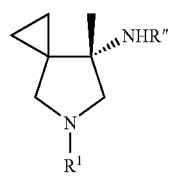

(XI)

(wherein R" represents a hydrogen atom or a protective group for amino group, and R¹ represents an aralkyl group which may have a substituent).

A compound represented by formula (XII):

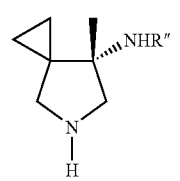

(XII)

(wherein R" represents a hydrogen atom or a protective group for amino group).

EFFECTS OF THE INVENTION

According to the production method of the present invention, by using (7S)-7-methyl-4-oxo-5-[(1R)-phenylethyl]-5-azaspiro[2.4]heptane-7-carboxylate ester derivative (VII) having a specific stereo-configuration (7S) as a synthesis intermediate, an optically active 7-amino-7-methyl-5-azaspiro[2.4]heptane derivative can be effectively produced in a simple manner, which is a useful starting material for constructing a 7-position substituent for a quinolonecarboxylic acid antibacterial agent (corresponds to 10-position in case of pyridobenzoxazinecarboxylic acid derivative) exhibiting excellent antibacterial activity, suitable pharmacokinetics and high safety.

In addition, according to the present invention, a 7-amino-7-methyl-5-azaspiro[2.4]heptane derivative having a specific stereo-configuration (7S), which is an important compound for expressing excellent antibacterial activity, suitable in vivo behavior and high safety, can be effectively produced in a simple manner, and optically active intermediate compounds therefor can be also provided. Furthermore, the present inventors have elucidated that, among 7-amino-7-methyl-5-azaspiro[2.4]heptane derivative enantiomers according to the present invention and disclosed in Japanese Patent Application No. 2005-146386, a 7S form serves as a substituent of a quinolonecarboxylic acid (pyridobenzoxazinecarboxylic acid) derivative providing higher antibacterial activity as compared with a 7R form.

BEST MODES FOR CARRYING OUT THE INVENTION

Figure 1:
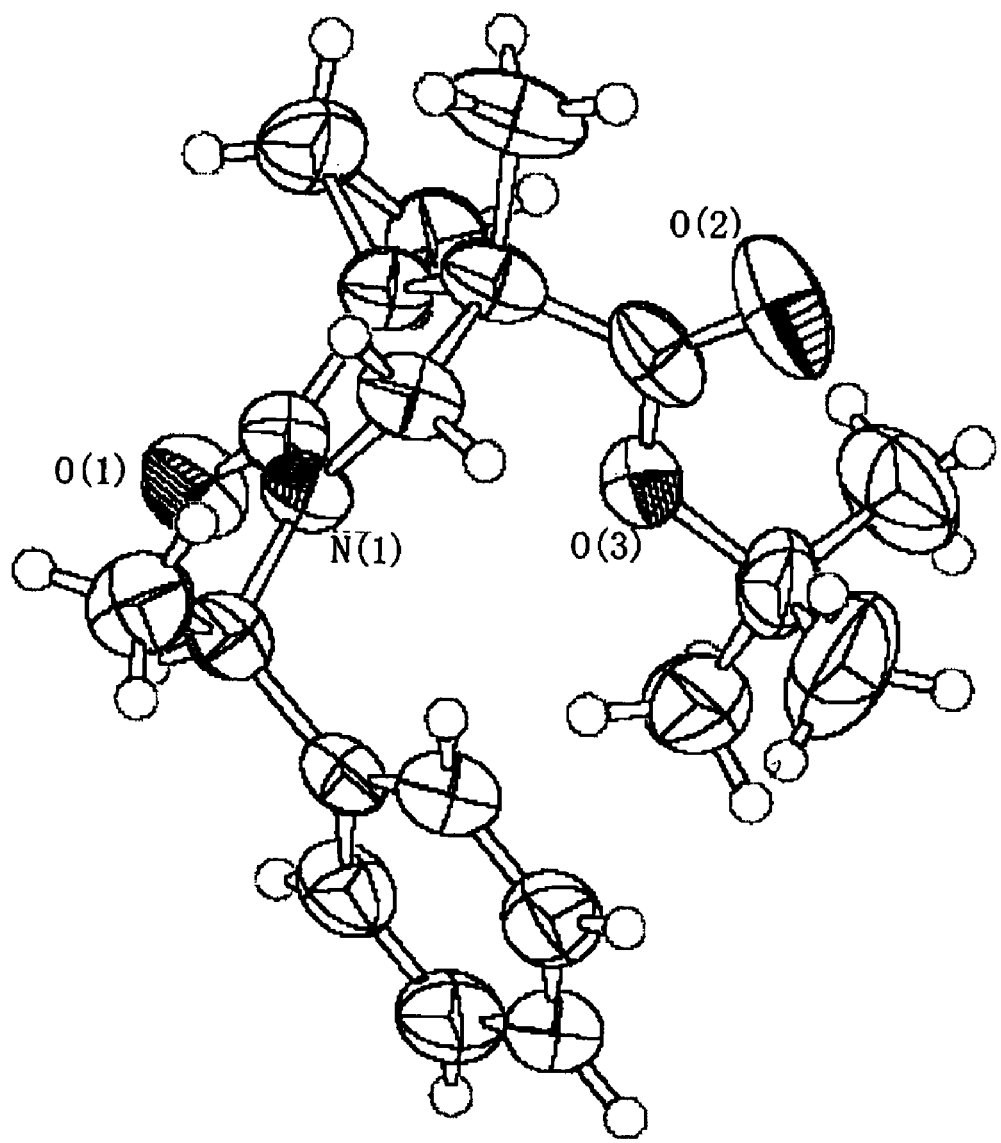
FIG. 1 Results of X-ray structural analysis of the compound produced in Example 5.

Each steps of the production method according to the present invention will hereinafter be described in detail.

Step A: Step 1 to Step 5 [compound (I) to compound (VII)]:

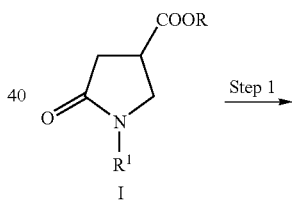

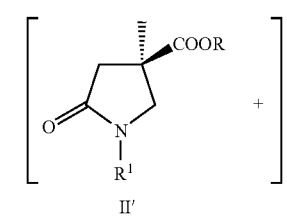

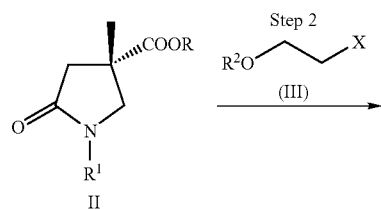

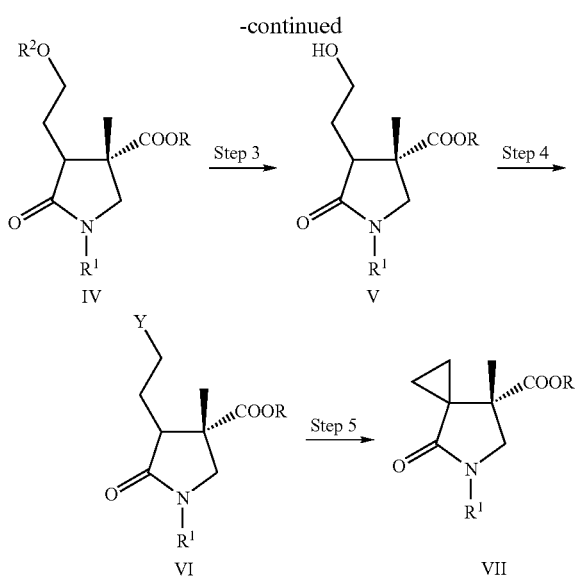

(wherein R, R¹, R², X and Y have the same meanings as defined above).

Step 1:

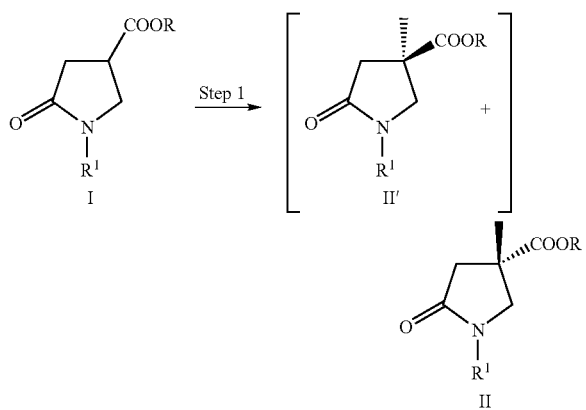

(wherein R, R¹, R', X and Y have the same meanings as defined above).

In Step 1, a compound represented by formula (I) (hereinafter the compound may be denoted by "compound (I)", and the same convention will be applied to compounds of other numbers) is reacted, in the presence of a base, with an appropriate methylating reagent which is generally employed in methylation of active methylene (or methine), to produce compound (II). Note that compound (I) may be produced through a method disclosed in Journal of Medicinal Chemistry, Vol. 30, No. 10, p.p. 1711 (1987).

In the above formulas, R is a group which can form a carboxylate ester. Examples of R include an aryl group which may have a substituent, an aralkyl group which may have a substituent, a C1 to C6 alkyl group which may have a substituent, and a chiral auxiliary which forms an optically active ester (—COOR).

Examples of the aryl group represented by R include a phenyl group and a naphthyl group. These groups may have, as a substituent, a halogen atom, a C1 to C6 alkoxy group, a C1 to C6 alkyl group, or a nitro group.

The aralkyl group represented by R is particularly preferably a group having a benzyl moiety. Specific examples thereof include a benzyl group, a p-nitrobenzyl group, a p-methoxybenzyl group, and a triphenylmethyl group.

The C1 to C6 alkyl group represented by R may be a linear or a branched alkyl group. Specific examples thereof include methyl, ethyl, propyl, isopropyl, n-butyl, and tert-butyl. The alkyl group may have one or more substituents such as a halogen atom and a C1 to C6 alkoxy group.

No particular limitation is imposed on the chiral auxiliary, so long as the auxiliary can forms an optically active carboxylate ester (—COOR). Specific examples of the chiral auxiliary include a (–)-menthyl group, a (–)-8-phenylmenthyl group, a (+)-neomenthyl group, a (S)-pantolacton-2-yl group, a (–)-bornyl, a 1-(R)-phenylethyl group, and a 1-(S)-phenylethyl group, which are so-called substituents derived from optically active alcohols. Other than these groups, the chiral auxiliary further includes optically active alkyl groups having a chain, cyclic or polycyclo structure and optically active aralkyl groups. Alternatively, the group R may be referred to as an optically active protective group for carboxy group.

R¹ represents an aralkyl group which may have a substituent. Specific examples thereof include aralkyl groups having no asymmetric carbon atom therein such as a benzyl group, a p-nitrobenzyl group, a diphenylmethyl group and a triphenylmethyl group, and optically active aralkyl groups having a asymmetric carbon atom therein such as a 1-(R)-phenylethyl group, 1-(S)-phenylethyl group, a 1-(R)-(1-nahpthyl)ethyl group and 1-(S)-(1-nahpthyl)ethyl group. Among them, preferred are a benzyl group, and an optically active aralkyl group, specifically a 1-(R)-phenylethyl group and a 1-(S)-phenylethyl group.

Combination of R and R¹ will next be described. When R¹ is an optically active aralkyl group (e.g., a 1-(R)-phenylethyl group or a 1-(S)-phenylethyl group), R is preferably a C1 to C6 alkyl group. Particularly, a tert-butyl group is preferred from a viewpoint such as easy isolation/purification of reaction products. When R¹ is an aralkyl group having no asymmetric carbon atom, typically a benzyl group, a chiral auxiliary which can form an optically active carboxylate ester is preferably employed as R¹, from a viewpoint such as easy isolation/purification of reaction products. Examples of preferred substituents R include generally employed chiral auxiliaries such as a (–)-menthyl group, a (–)-8-phenylmenthyl group, and a 1-(R)-phenylethyl group.

In Step 1, compound (I) is reacted, in the presence of a base, with an appropriate methylating reagent which is generally employed in methylation of active methylene (or methine). Specific examples of the methylating reagent employed in the reaction include methyl halide and dimethyl disulfate. More preferably, methyl iodide is employed.

In the reaction of Step 1, an organic base or an inorganic base may be used. Examples of the organic bases include organometallic compounds such as lithium diisopropylamide, lithium bistrimethylsilylamide, lithium 2,2,6,6-tetramethylpiperidine, n-butyllithium, sec-butyllithium, sodium bistrimethylsilylamide and potassium bistrimethylsilylamide; alkylamines such as triethylamine and N,N-diisopropylethylamine; saturated and unsaturated nitrogen-containing heterocyclic compounds such as 4-methylmorpholine, 1,8-diazabicyclo[5.4.0]-7-undecene and pyridine; and alkali metal alkoxides such as sodium methoxide, sodium ethoxide, sodium tert-butoxide and potassium tert-butoxide. Examples of the inorganic bases include alkali metal hydroxides such as sodium hydroxide and potassium hydroxide; alkali metal hydrides such as sodium hydride and potassium hydride; alkali amides such as sodium amide; alkali metal carbonates such as sodium carbonate and potassium carbonate; and alkali metal hydrogencarbonates such as sodium hydrogencarbonate and potassium hydrogencarbonate. Among these bases, examples of particularly preferred bases include organometallic compounds such as lithium diisopropylamide, lithium bistrimethylsilylamide, sodium bistrimethylsilylamide, and potassium bistrimethylsilylamide; and alkali metal hydrides such as sodium hydride and potassium hydride.

The reaction of Step 1 is performed in a solvent. No particular limitation is imposed on the reaction solvent, so long as the solvent does not inhibit the reaction. Examples of the solvent employed in Step 1 include ether solvents such as tetrahydrofuran, 1,4-dioxane, diethyl ether, diisopropyl ether and 1,2-dimethoxyethane; amide solvents such as N,N-dimethylacetamide, N,N-dimethylformamide and N-methyl-2-pyrrolidone; aromatic hydrocarbon solvents such as benzene, toluene and xylene; and other solvents (e.g., dimethyl sulfoxide). When an alkali metal alkoxide such as sodium methoxide, sodium ethoxide, sodium tert-butoxide or potassium tert-butoxide is employed as a base, an alcoholic solvent such as methanol, ethanol or tert-butanol may also be employed. These solvents may be used in combination. Among them, particularly preferred solvent may include tetrahydrofuran, 1,4-dioxane, N,N-dimethylformamide, and the like.

The reaction temperature, which varies in accordance with the type of the base and the employed solvent, can range from −78° C. to the boiling point of the solvent, preferably from −78° C. to room temperature, or from ice-cooling temperature to the boiling point of the solvent.

Through methylation, an antipodal isomer mixture is formed. Each antipode can be readily isolated by means of a silica gel column. As disclosed in the aforementioned Non-Patent Document, a methylated product from a methyl ester is difficult to isolate by means of a silica gel column. However, surprisingly, the inventors have found that, when a tert-butyl ester is employed, the corresponding methylated compound can be readily separated by means of a silica gel column. In the present invention, the antipode having coordination of interest is an antipode of higher polarity, when eluted with silica gel column with a hexane-ethyl acetate mixture as an eluent.

Step 2:

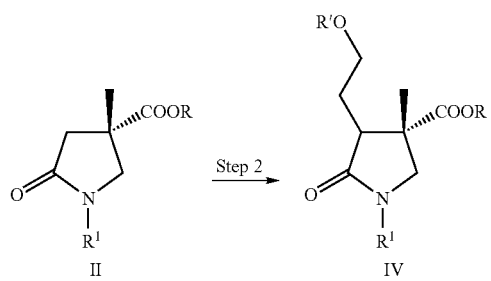

(wherein R, $R^1$, and R' have the same meanings as defined above).

In Step 2, compound (II) is reacted with a compound represented by formula (III):

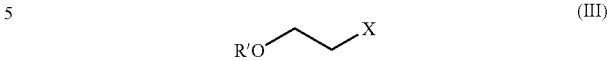

(wherein R, $R^1$, and X have the same meanings as defined above), to produce compound (IV).

R' may be a protective group for hydroxy group. No particular limitation is imposed on the species of R', so long as R' is a typically employed protective group. Examples of such a protective group include acyl groups such as acetyl, methoxyacetyl, trifluoroacetyl, chloroacetyl, pyvaloyl, formyl and benzoyl; alkyl and aralkyl groups such as tert-butyl, benzyl, p-methoxybenzyl, p-nitrobenzyl and triphenylmethyl; ether groups such as methoxymethyl, tert-butoxymethyl, tetrahydropyranyl and 2,2,2-trichloroethoxymethyl; and substituted silyl groups such as trimethylsilyl, isopropyldimethylsilyl, tert-butyldimethysilyl, tribenzylsilyl and tert-butyldiphenylsilyl. Among these protective groups, a protective group which neither leaves nor decomposes in a reaction mixture in the presence of a base is preferred. Such a protective group is preferably an aralkyl group, an ether group or a substituted silyl group. Specific examples of the protective group include a benzyl group which may have a substituent, a methoxymethyl group, a tetrahydropyranyl group, a tert-butyldimethylsilyl group and a tert-butyldiphenylsilyl group.

X represents a halogen atom or a leaving group other than halogen atom. Among halogen atoms, a chlorine atom, a bromine atom, and an iodine atom are preferred, with an iodine atom being particularly preferred. When X is a leaving group, it may be a leaving group for nucleophilic substitution. Examples include substituted sulfonyloxy groups such as a methanesulfonyloxy group, a trifluorobenzenesulfonyloxy group, a toluenesulfonyloxy group, and a benzenesulfonyoxy group. Among halogen atoms, an iodine atom is particularly preferred as X.

The reaction of Step 2 is performed in the presence of a base, and an organic base or an inorganic base may be employed. Examples of the organic bases include organometallic compounds such as lithium diisopropylamide, lithium bistrimethylsilylamide, lithium 2,2,6,6-tetramethylpiperidine, n-butyllithium, sec-butyllithium, sodium bistrimethylsilylamide and potassium bistrimethylsilylamide; alkylamines such as triethylamine and N,N-diisopropylethylamine; saturated and unsaturated nitrogen-containing heterocyclic compounds such as 4-methylmorpholine, 1,8-diazabicyclo[5.4.0]-7-undecene and pyridine; and alkali metal alkoxides such as sodium methoxide, sodium ethoxide, sodium tert-butoxide and potassium tert-butoxide. Examples of the inorganic bases include alkali metal hydroxides such as sodium hydroxide and potassium hydroxide; alkali metal hydrides such as sodium hydride and potassium hydride; and alkali amides such as sodium amide. Among these bases, examples of particularly preferred bases include organometallic compounds such as lithium diisopropylamide, lithium bistrimethylsilylamide, sodium bistrimethylsilylamide, and potassium bistrimethylsilylamide.

The reaction of Step 2 is performed in a solvent. Examples of the solvent employed in Step 2 include aromatic hydrocarbon solvents such as benzene, toluene and xylene; ether solvents such as tetrahydrofuran, 1,4-dioxane, diethyl ether and 1,2-dimethoxyethane; amide solvents such as N,N-dimethylacetamide, N,N-dimethylformamide and N-methyl-2-pyrrolidone; and other solvents (e.g., liquid ammonia or dimethyl sulfoxide). When an alkali metal alkoxide such as sodium methoxide, sodium ethoxide, sodium tert-butoxide or potassium tert-butoxide is employed as a base, an alcoholic solvent such as methanol, ethanol or tert-butanol may also be employed. These solvents may be used in combination. Among them, particularly preferred solvent may include tetrahydrofuran, toluene, N,N-dimethylformamide, and the like.

The reaction temperature, which varies in accordance with the type of the base and the employed solvent, can range from −78° C. to the boiling point of the solvent, preferably from −78° C. to room temperature.

Step 3:

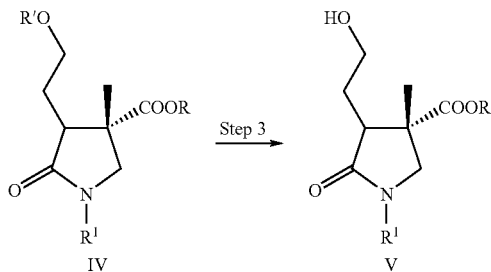

IV    V (wherein R, R$^1$, and R' have the same meanings as defined above).

In Step 3, the protective group for hydroxy group is removed from compound (IV) to produce compound (V).

Removal of the protective group in Step 3 may be performed through a generally employed removal method. No particular limitation is imposed on the deprotection method (reagent, solvent, and reaction conditions), and any method may be employed so long as it is suited for the employed protective group and does not affect a 3-position ester moiety (COOR) of compound (IV) and compound (V).

Exemplary deprotection conditions will next be described in detail with respect to particularly preferred protective groups for hydroxy group of compound (III), namely a benzyl group, a methoxymethyl group, a tetrahydropyranyl group, a tert-butyldimethylsilyl group and tert-butyldiphenylsilyl group.

An aralkyl group such as a benzyl group may be deprotected through catalytic reduction or Birch's reduction.

An ether group such as a methoxymethyl group may be deprotected through treatment with an acid appropriately selected from among inorganic and organic acids including hydrochloric acid, sulfuric acid, nitric acid, hydrofluoric acid, hydrobromic acid, hydroiodic acid, toluenesulfonic acid, methanesulfonic acid, trifluoroacetic acid, and trichloroacetic acid. In this case, an acid which does not cause hydrolysis of an ester (COOR) must be selected.

A substituted silyl group such as a tert-butyldimethylsilyl group may be deprotected by an acid or a fluoride anion. In this case, the acid may be selected from acetic acid, hydrochloric acid, hydrofluoric acid, etc. in accordance with the properties of the silyl group, but an acid which does not cause hydrolysis of an ester (COOR) must be selected. The source of fluoride anion may include tetrabutylammonium fluoride.

Deprotection reaction may be performed in an appropriate solvent in which compound (IV) and compound (V) can be dissolved. The reaction temperature, which may be selected in accordance with the type and concentration of acid and deprotecting reagent to be used, type of the solvent, etc., may be appropriately selected from a range of −30 to 100° C.

Step 4:

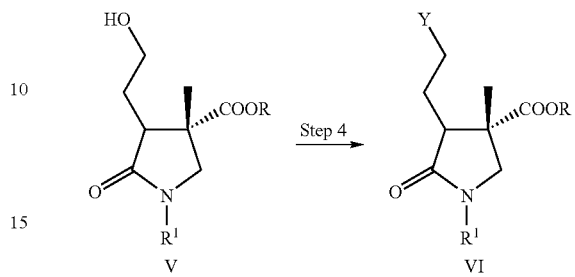

V    VI (wherein R, R$^1$, R', and Y have the same meanings as defined above).

In Step 4, the hydroxy group of compound (V) is transformed to a halogen atom or a leaving group other than halogen atom employed in nucleophilic substitution, to produce compound (VI).

Y represents a halogen atom or a leaving group other than halogen atom. Among halogen atoms, a bromine atom and an iodine atom are preferred, with an iodine atom being particularly preferred. When Y is a leaving group other than halogen atom, the leaving group is a leaving group for nucleophilic substitution. Examples of the leaving group include a substituted sulfonyloxy group such as a trifluoromethanesulfonyl group, a methanesulfonyloxy group, a toluenesulfonyloxy group, and a benzenesulfonyoxy group. Of these, a benzenesulfonyoxy group is particularly preferred. In other words, an iodine atom and a benzenesulfonyoxy group are particularly preferred as Y.

The halogenation step of hydroxy group (Step 4) will next be described in detail. In halogenation of an alcoholic hydroxy group, either direct halogenating or halogenation via alkyl halide or a leaving group may be employed.

One exemplary method for brominating an alcoholic hydroxy group is bromination using hydrogen bromide, for example, 48% hydrobromic acid. In this case, an appropriate amount of concentrated sulfuric acid is added so as to prevent side reaction producing ether. Alternatively, hydrobromic acid may be generated in a reaction mixture including sulfuric acid and lithium bromide or potassium bromide. Bromination may also be performed by use of phosphorus tribromide, a Vilsmeier reagent prepared from an amide and an inorganic acid bromide, or triphenylphosphine dibromide. In these alternative methods, bromination is preferably performed generally by use of N,N-dimethylformamide as a solvent.

One exemplary method for iodine-substitution of an alcoholic hydroxy group is iodation by use of hydrogen iodide. Specifically, iodation may be performed by use of hydroiodic acid, potassium iodide-phosphoric acid, or a potassium iodide-hydrogen fluoride pyridine solution. Alternatively, iodation may also be performed by use of phosphorus triiodide or diphosphorus tetraiodide. In a preferred method, a hydroxy group may be transformed to a leaving group for nucleophilic substitution such as a substituted sulfonyloxy group, typically a methanesulfonyloxy group or a toluenesulfonyloxy group, and the transformed moiety may be reacted with lithium iodide, sodium iodide, or potassium iodide, in a solvent such as tetrahydrofuran, acetone or N,N-dimethylformamide.

Meanwhile, in Step 4, introduction of a leaving group for nucleophilic substitution such as a substituted sulfonyloxy group is performed by reacting with a substituted sulfonyl chloride or a substituted sulfonic anhydride in the presence of an organic base such as triethylamine, pyridine or 4-dimethylpyridine. No particular limitation is imposed on the solvent used in the reaction, so long as it does not inhibit the reaction, and a chlorine-containing solvent such as dichloromethane or 1,2-dichloroethane, tetrahydrofuran, toluene, etc. may be used. When a base such as pyridine is used, the base may also serve as the solvent.

The reaction temperature, which varies in accordance with the type of the base and the employed solvent, generally can range from $-78°$ C. to $100°$ C., preferably from $-30°$ C. to room temperature.

Step 5:

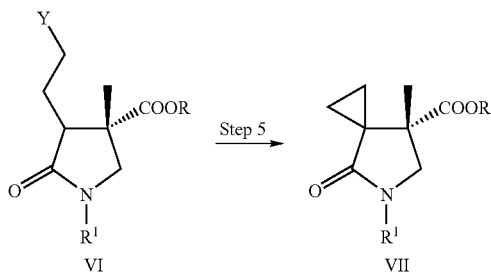

(wherein R, $R^1$, and Y have the same meanings as defined above).

In Step 5, compound (VI) is cyclized in the presence of a base so as to construct a spirocyclic structure to form compound (VII).

Step 5 is a step of producing a compound (VII) through intramolecular alkylation of a compound (VI) in which Y is a halogen atom or a leaving group other than halogen atom. The intramolecular alkylation may be performed in the presence of a base. In Step 5, an organic base or an inorganic base may be employed. Examples of the organic bases include organometallic compounds such as lithium diisopropylamide, lithium bistrimethylsilylamide, lithium 2,2,6,6-tetramethylpiperidine, n-butyllithium, sec-butyllithium, sodium bistrimethylsilylamide and potassium bistrimethylsilylamide; alkylamines such as triethylamine and N,N-diisopropylethylamine; saturated and unsaturated nitrogen-containing heterocyclic compounds such as 4-methylmorpholine, 1,8-diazabicyclo[5,4,0]-7-undecene and pyridine; and alkali metal alkoxides such as sodium methoxide, sodium ethoxide, sodium tert-butoxide and potassium tert-butoxide. Examples of the inorganic bases include alkali metal hydroxides such as sodium hydroxide and potassium hydroxide; alkali metal hydrides such as sodium hydride and potassium hydride; and alkali amides such as sodium amide. Among these bases, examples of particularly preferred bases include organometallic compounds such as lithium diisopropylamide, lithium bistrimethylsilylamide, sodium bistrimethylsilylamide, and potassium bistrimethylsilylamide.

The reaction of Step 5 is performed in a solvent. Examples of the solvent employed in Step 5 include aromatic hydrocarbon solvents such as benzene, toluene and xylene; ether solvents such as tetrahydrofuran, 1,4-dioxane, diethyl ether and 1,2-dimethoxyethane; amide solvents such as N,N-dimethylacetamide, N,N-dimethylformamide and N-methyl-2-pyrrolidone; and other solvents (e.g., liquid ammonia or dimethyl sulfoxide). When an alkali metal alkoxide such as sodium methoxide, sodium ethoxide, sodium tert-butoxide or potassium tert-butoxide is employed as a base, an alcoholic solvent such as methanol, ethanol or tert-butanol may also be employed. These solvents may be used in combination. Among them, tetrahydrofuran, toluene, N,N-dimethylformamide, etc. are particularly preferred as the solvent.

The reaction temperature, which varies in accordance with the type of the base and the employed solvent, can range from $-78°$ C. to the boiling point of the solvent, preferably from $-78°$ C. to room temperature.

Instead of the compound (III) employed in Step 3, when a compound represented by formula (III'):

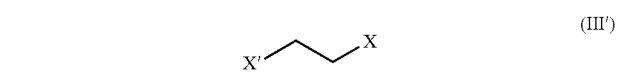

and (wherein X has the same meaning as defined above, and X' represents a group selected from a halogen atom which is identical to or different from the halogen atom used as X, and a leaving group other than the halogen atom) is employed to produce compound (VII). Compound (VII) can be produced through one single (continuous and minimum) step, instead of three steps of Steps 3 to 5 as described above. Compound (III') is a compound in a halogen or a leaving group is replaced for an $R^{10}$ group of compound (III). Compound (III') is employed in the following reaction:

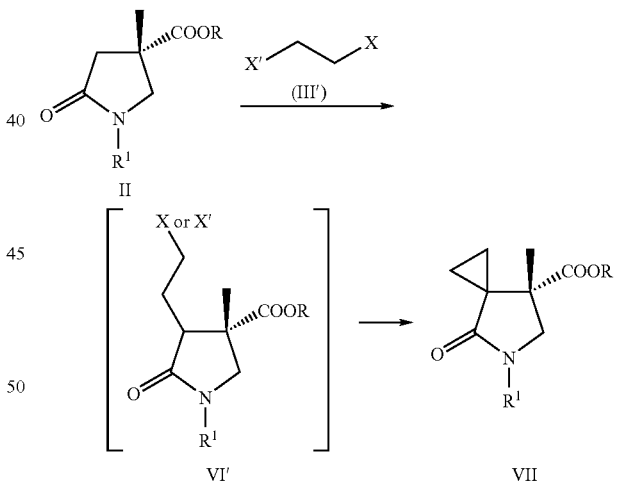

(wherein R, $R^1$, X, and X' have the same meanings as defined above).

This reaction is performed in the presence of a base under reaction conditions as described above with respect to Step 3 or 5.

Examples of compound (III') which may be employed in the aforementioned reaction include 1,2-dibromoethane, 1,2-diiodoethane, 1-bromo-2-chloroethane, 2-chloroethyl methanesulfonate, 2-chloroethyl toluenesulfonate, 2-iodoethyl methanesulfonate, and 2-iodoethyl benzenesulfonate.

Step B: Alternative synthesis method for compound (VII)

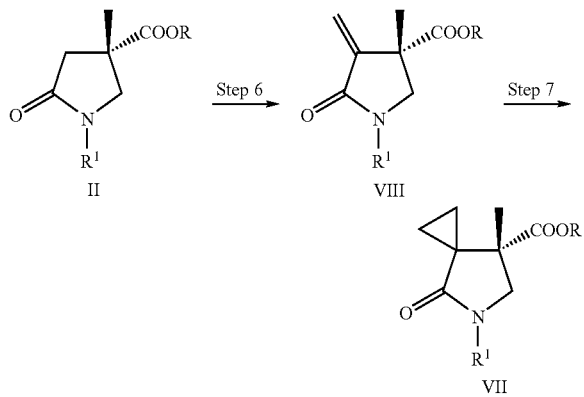

Step 6:

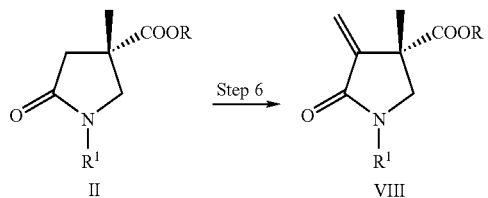

(wherein R and R¹ have the same meanings as defined above)

In Step 6, an exo-methylene group is introduced to compound (II) to produce compound (VIII). Through combination of Step 6 and the subsequent step, an alternative method for producing compound (VII) is provided.

In Step 6, an exo-methylene group is introduced to the α-position to the amide (active methylene). Examples of reactions for the introduction include a method employing N,N-dimethylmethyleneammonium iodide (Eschenmoser salt) in the presence of a base; a method including introduction of a phosphate ester and Horner-Emmons reaction with formaldehyde; a method employing methylmethoxy magnesium carbonate; and a method including hydroxymethylation and dehydration.

More specifically, in Step 6, the α-position to the amide is formylated in the presence of a base, and the product is reacted with formaldehyde to conduct decarbonyl-methylation.

The reaction of Step 6 is performed in the presence of a base. Examples of employable organic bases include organometallic compounds such as lithium diisopropylamide, lithium bistrimethylsilylamide, lithium 2,2,6,6-tetramethylpiperidine, n-butyllithium, sec-butyllithium, sodium bistrimethylsilylamide, and potassium bistrimethylsilylamide; and alkali metal alkoxides such as sodium methoxide, sodium ethoxide, sodium tert-butoxide, and potassium tert-butoxide. Among these bases, examples of particularly preferred bases include organometallic compounds such as lithium diisopropylamide, lithium bistrimethylsilylamide, sodium bistrimethylsilylamide, and potassium bistrimethylsilylamide.

The reaction of Step 6 is performed in a solvent. Examples of the solvent employed in Step 6 include aromatic hydrocarbon solvents such as benzene, toluene and xylene; ether solvents such as tetrahydrofuran, 1,4-dioxane, diethyl ether and 1,2-dimethoxyethane; and amide solvents such as N,N-dimethylacetamide, N,N-dimethylformamide and N-methyl-2-pyrrolidone. When an alkali metal alkoxide such as sodium methoxide, sodium ethoxide, sodium tert-butoxide or potassium tert-butoxide is employed as a base, an alcoholic solvent such as methanol, ethanol or tert-butanol may also be employed. These solvents may be used in combination. Among them, tetrahydrofuran, toluene, N,N-dimethylformamide, etc. are particularly preferred as the solvent.

The reaction temperature, which varies in accordance with the type of the base and the employed solvent, can range from −78° C. to the boiling point of the solvent, preferably from −780° C. to room temperature.

Step 7:

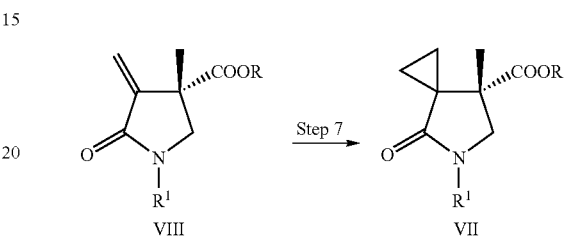

(wherein R and R¹ have the same meanings as defined above)

In Step 7, a methylene group is cyclo-added to the double-bonded exo-methylene moiety included in the enamide moiety of compound (VIII) to construct a cyclopropane ring, whereby compound (VII) is produced.

Examples of reactions achieving Step 7 include a carbene-carbenoid reaction employing a diazomethane-transition metal catalyst, a diiodomethane-diethylzinc (Simmons-Smith reagent), etc.; and Michael addition employing a sulfur ylide (Corey reagent).

Specifically, when a carbenoid reaction using a diazomethane-transition metal catalyst system is employed, compound (VIII) is dissolved in a solvent, and the catalyst is added to the solution. Subsequently, a diazomethane diethyl ether solution which has been prepared through an ordinary method is added to the reaction mixture to allow to react.

Examples of the catalyst which may be employed in the above reaction include palladium(II) acetate and palladium(II) acetylacetonate.

Examples of the reaction solvent employed in this reaction include hydrocarbon solvents such as n-hexane; ether solvents such as tetrahydrofuran, 1,4-dioxane, 1,2-dimethoxyethane, and diethyl ether; and halogen-containing solvents such as dichloromethane and dichloroethane. These solvents may be used in combination.

The reaction temperature, which varies in accordance with the employed solvent, may be from −20° C. to 0° C.

When a carbene reaction using a Simmons-Smith reagent and other material is employed, specifically, compound (VIII) is dissolved in a solvent, and a methylene halide such as diiodomethane or chloroiodomethane is used as a carbon source. The mixture is allowed to react in the presence of a metallic reagent such as diethylzinc, zinc-copper, samarium-mercury(II) chloride, or a trialkylaluminum such as trimethyl aluminum.

In this case, diiodomethane is preferred as a methylene halide, and diethylzinc and zinc-copper are preferred as a metallic reagent.

Examples of the reaction solvent include aliphatic hydrocarbon solvents such as n-hexane; aromatic hydrocarbon solvents such as benzene, toluene and xylene; ether solvents such as tetrahydrofuran, 1,4-dioxane, 1,2-dimethoxyethane and diethyl ether; and halogen-containing solvents such as dichloromethane and dichloroethane. These solvents may be used in combination.

The above reaction may be performed with addition of trifluoroacetic acid.

The reaction temperature, which varies in accordance with the type of the base and the employed solvent, may be from −78° C. to the boiling point of the solvent.

According to Step A, since optically active form (II) can be transformed to compound (VII) with maintaining its stereo-configuration, compound (VII) having high optical purity can be synthesized. As compared with Step A, Step B can provide a target compound (VII) through much more simple manner and fewer steps. Both Steps A and B do not involve a reagent or an operation which is particularly unsuitable for large-scale production of industrial scale. Therefore, Step B, which includes fewer steps, is more advantageous than Step A.

Since compound (VII) has high crystallinity, a 7S absolute configuration of the asymmetric carbon at the 7-position (methyl substitution position) has been successfully elucidated through X-ray crystallographic structural analysis.

The analysis has revealed that the configuration which provides a relevant quinolone compound exhibiting more excellent physiological activity is 7S.

Step C: Introduction of Amino Group

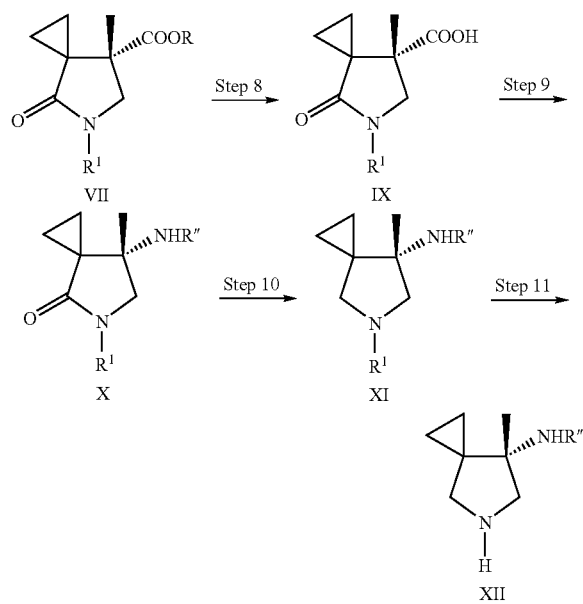

A step of introducing an amino group into compound (VII) will next be described.

Step 8:

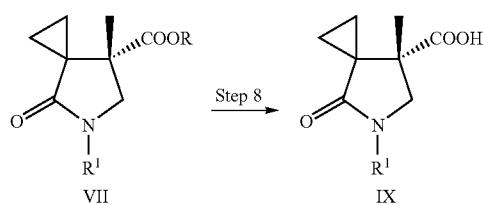

(wherein R and R¹ have the same meanings as defined above)

In Step 8, ester compound (VII) is hydrolyzed to produce compound (IX), which is a free carboxylic acid compound.

No particular limitation is imposed on the hydrolysis performed in Step 8, and any reaction may be employed so long as it can be carried out under basic or acidic conditions generally employed for ester hydrolysis, or under hydrogenolysis conditions. When R is an aryl group which may have a substituent or a C1 to C6 alkyl group which may have a substituent, hydrolysis is preferably performed under basic or acidic hydrolysis conditions, whereas, when R is a C7 to C9 aralkyl group which may have a substituent, hydrolysis is preferably performed under hydrogenolysis conditions.

When hydrolysis is performed under acidic conditions, hydrochloric acid or sulfuric acid is generally employed as an acid. Alternatively, a Lewis acid; e.g., boron trichloride, may also be used. The solvent for hydrolysis is suitably acetic acid, formic acid or a mixture thereof with water. The ester suitably hydrolyzed under acidic conditions is a tert-butyl ester. In the hydrolysis of such a tert-butyl ester, trifluoroacetic acid or p-toluenesulfonic acid may also be used as an acid. Although the acid may also serve as a solvent, a solvent such as dichloromethane may be employed. Alternatively, a combination of Lewis acid and thiol or sulfide may also be employed.

When hydrolysis is performed under basic conditions, i.e., alkaline hydrolysis conditions, an appropriate concentration of an aqueous solution of an alkali such as sodium hydroxide, potassium hydroxide, lithium hydroxide or barium hydroxide is generally employed. The reaction solvent is preferably an alcoholic solvent such as methanol, ethanol, tetrahydrofuran or ethylene glycol, or a mixture thereof with water. The reaction temperature is suitably from −15 to 100° C., preferably from 0 to 50° C. The hydrolysis may be performed with addition of an aqueous alkaline solution or a small amount of surfactant. Examples of the surfactant include tetraethylammonium chloride, tetrabutylammonium bromide, and tetrabenzylammonium bromide. After completion of the hydrolysis, a free carboxylic acid compound can be produced by use of a mineral acid such as hydrochloric acid, sulfuric acid, or acetic acid, or an acidic ion exchange resin.

An aralkyl ester having a benzyl moiety such as a benzyl ester, a benzhydryl ester, or a 1-(R)-phenylethyl ester is cleaved through catalytic hydrogenolysis reaction in the presence of a catalyst to produce a carboxylic acid compound. In the catalytic hydrogenolysis reaction, a palladium-carbon catalyst is preferably employed as a catalyst. Specifically, a reaction substrate is dissolved in a solvent such as methanol, ethanol or tetrahydrofuran, and the solution is subjected to hydrogenolysis in a hydrogen atmosphere under ambient pressure (1 atm) to appropriately pressurized conditions at room temperature to 50° C. Alternatively, reduction in liquid ammonia with metallic lithium also produces a carboxylic acid compound.

The thus-synthesized compound (IX):

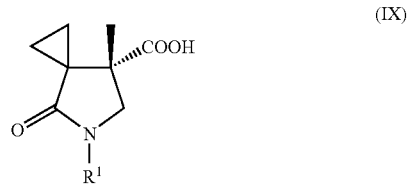

(wherein R¹ has the same meaning as defined above) may be a free carboxylic acid or may be transformed to a carboxylate salt. Examples of the carboxylate salt include inorganic and organic salts, such as, for example, alkali metal salts such as a lithium salt, a sodium salt and a potassium salt; alkaline earth metal salts such as a magnesium salt and a calcium salt; an ammonium salts; and a triethylamine salt. These carboxylate salts may be a hydrate thereof.

Step 9:

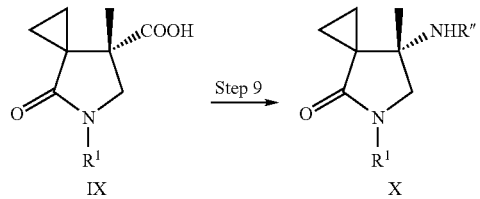

(wherein $R^1$ has the same meaning as defined above, and R" represents a hydrogen atom or a protective group for amino group.).

In Step 9, the carboxy group of compound (IX) is rearranged to a (substituted) amino group to produce compound (X).

Rearrangement of the carboxy group to a (substituted) amino group carried out in Step 9 may be performed through some known methods. In a preferred mode, a carboxylic acid is transformed to an acid azide, and the azide is thermally rearranged to an isocyanate, followed by hydrolyzing the isocyanate to form an amine. This method is known as Curtius rearrangement.

Transformation of a carboxylic acid to an acid azide may be performed by adding a C1 to C6 alkyl chloroformate to a carboxylic acid compound in the presence of a base, and reacting the formed active ester with an aqueous sodium azide solution. Examples of preferred alkyl chloroformates employable in the reaction include methyl chloroformate, ethyl chloroformate, and butyl chloroformate. Examples of the base employed in the reaction include organic bases such as triethylamine and diisopropylethylamine; and inorganic bases such as sodium hydroxide, potassium hydroxide, sodium carbonate, and potassium carbonate. Preferably, the reaction is performed in a solvent, for example, acetone, dichloromethane, tetrahydrofuran, toluene, or a mixture thereof, at −20° C. to room temperature.

The acid azide is heated in a solvent that is inert to the azide or to an isocyanate to be formed, at the boiling point of the solvent, to rearrange the azide to an isocyanate. Examples of preferred inert solvents include toluene, xylene, benzene, and a mixture thereof.

For performing the direct production of an isocyanate from the aforementioned carboxylic acid via an acid azide, one preferred method is a simple procedure employing diphenylphosphoryl azide (DPAA) in an appropriate solvent in the presence of a base.

Subsequently, the isocyanate formed through the aforementioned appropriate method may be hydrolyzed in the presence of an acid, at −5° C. to room temperature or with heating under reflux conditions, or hydrolyzed in the presence of an alkali at room temperature to 110° C., to produce substituted amine compound. Examples of the acid preferably employed in hydrolysis under acidic conditions include hydrochloric acid, hydrobromic acid, and sulfuric acid, which are in the form of aqueous solution having an appropriate concentration. Through hydrolysis with any of these acids, a free amine or an acid addition salt thereof can be produced. Examples of the alkali preferably employed in hydrolysis under alkaline conditions include sodium hydroxide and potassium hydroxide, which are in the form of aqueous solution having an appropriate concentration.

Through reacting the isocyanate in an alcoholic solvent or in a solvent inert to isocyanate such as toluene, xylene, or benzene to which an alcohol is added, a carbamate derivative in which the amino group is protected by an alkoxycarbonyl group can be directly produced. This reaction may be performed in the presence of a base such as triethylamine or sodium alkoxide. Examples of the alcohol include methanol, ethanol, isopropanol, butanol, tert-butanol, and benzyl alcohol. Depending on the alcohol used, corresponding carbamates; i.e., methyl carbamate, ethyl carbamate, isopropyl carbamate, butyl carbamate, tert-butyl carbamate, and benzyl carbamate can be produced. Among these alcohols, tert-butanol is particularly preferred. Theoretically, the amount of alcohol required in the reaction is 1 fold by mole or more with respect to carboxylic acid. However, a large excess amount of alcohol can be generally used.

A specific mode of the Curtius rearrangement given as an exemplary method of rearranging a carboxylic acid to an amine carried out in Step 9 is also described in Examples. However, rearrangement reactions other than Curtius rearrangement may also be employed. For example, Hoffmann rearrangement in which a carboxylic acid is transformed to an amine via an acid amide (carbamoyl derivative) may be employed.

When R" in the compound (X):

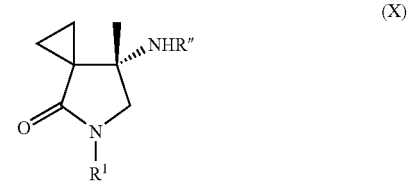

and (wherein $R^1$ and R" have the same meanings as defined above) which is produced in Step 9 is a hydrogen atom, the compound (X) may be present as a free amine or an acid addition salt thereof. Examples of the acid addition salt include inorganic salts and organic salts. Specific examples of the inorganic salts and the organic salts include inorganic acid salts such as a hydrochloride, a sulfate, a nitrate, a hydrobromide, a hydroiodide, and a phosphate; and organic acid salts such as a sulfonate (e.g., a mathanesulfonate, a benzenesulfonate, and a toluenesulfonate) and a carboxylate (e.g., an acetate, a citrate, a maleate, a fumarate, a lactate, and an oxalate). These acid addition salts may also be present as a hydrate thereof.

When R" is a protective group for amino group, no particular limitation is imposed on the type of the protective group, and any protective groups may be employed, so long as the group is generally employed and easy to protect and deprotect, and does not affect a subsequent step, or so long as the group itself is non-reactive. Such a protective group for amino group may be selected from groups generally employed protective groups; for example, an alkoxycarbonyl group which may have a substituent, an aralkyloxycarbonyl group which may have a substituent, an acyl group which may have a substituent, an aralkyl group which may have a substituent, and a substituted silyl group. Examples of the alkoxycarbonyl group which may have a substituent include methoxycarbonyl, ethoxycarbonyl, tert-butoxycarbonyl, and 2,2,2-trichloroethoxycarbonyl. Examples of the acyl group which may have a substituent include acetyl, methoxyacetyl, trifluoroacetyl, chloroacetyl, pivaloyl, formyl, and benzoyl. Examples of the aralkyloxycarbonyl group which may have a substituent include benzyloxycarbonyl, p-methoxybenzyloxycarbonyl, p-nitrobenzyloxycarbonyl. Examples of the substituted silyl group include trimethylsilyl, isopropyldimethylsilyl, tert-butyldimethylsilyl, tribenzylsilyl, tert-butyldimethylsilyl. Of these, as substituent R", an alkoxycarbonyl group which may have a substituent, an aralkyloxycarbonyl group which may have a substituent, and an acyl group which may have a substituent are preferred. More specifically, methoxycarbonyl, ethoxycarbonyl, tert-butoxycarbonyl, benzyloxycarbonyl, acetyl, trifluoroacetyl are preferred, with tert-butylcarbonyl being particularly preferred.

When deprotection is required, deprotection conditions are appropriately selected in accordance with the properties of protective group R".

Step 10:

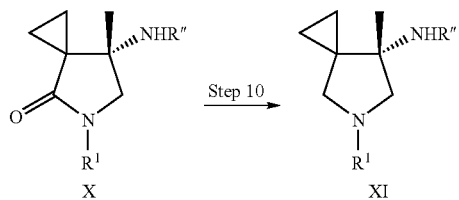

(wherein $R^1$ and R" have the same meanings as defined above)

In Step 10, compound (X) is treated under acid amide reduction condition to produce pyrrolidine compound (XI).

Reduction in Step 10 is generally performed by use of a metal hydride. Examples of the metal hydride include lithium aluminum hydride, a combination of sodium borohydride and a Lewis acid (e.g., sodium borohydride-tin(II) chloride), diborane, and a borane-tetrahydrofuran complex. Of these, lithium aluminum hydride and a borane-tetrahydrofuran complex are particularly preferred.

An inert solvent is used as a reaction solvent. Specifically, ether solvents such as diethyl ether, tetrahydrofuran, diisopropyl ether and 1,4-dioxane are preferred, with tetrahydrofuran being particularly preferred.

The reaction is performed at 0° C. to the boiling point of the solvent employed; i.e., the reflux temperature of the solvent. Preferably, the reaction is performed at room temperature to a temperature under reflux conditions.

In the aforementioned reduction of an acid amide by use of a metal hydride, the amino group of compound X may be free or protected. However, a compound (X) having a free amino group (R" is a hydrogen atom) is preferably used. When R' is a protective group for amino group, the protective group must be stable under the selected reduction conditions.

When R is a protective group for amino group, the protective group is selected from the same groups as described in detail in relation to Step 9. In order to facilitate isolation and purification of product (XI), in this Step 10, a protective group is introduced preferably after the reduction of the amide.

Alternatively, reduction of an acid amide may also be performed through transforming the carbonyl group of the amide to a thiocarbonyl group by use of an appropriate reagent to form a thioamide, and then desulfurizing it (e.g., by catalytic reduction). In such a case, the carbonyl group of the amide is transformed to a thiocarbonyl group generally by use of a Lawessons's reagent, and the reaction is performed in benzene or toluene under reflux conditions. Subsequently, desulfurization is preferably performed in a solvent such as methanol, ethanol, or tetrahydrofuran under hydrogen atmosphere by use of a Raney nickel catalyst. The reaction may also be performed in an alcoholic solvent such as ethanol in the absence of hydrogen gas.

The compound (XI):

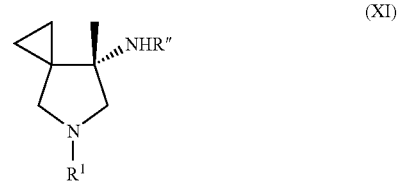

and (wherein $R^1$ and R" have the same meanings as defined above) produced in Step 10 may be present as a free amine (dibasic form) or an acid addition salt thereof. Examples of the acid addition salt include inorganic salts and organic salts. Specific examples of the inorganic salts and the organic salts include inorganic acid salts such as a hydrochloride, a sulfate, a nitrate, a hydrobromide, a hydroiodide, and a phosphate; and organic acid salts such as a sulfonate (e.g., a mathanesulfonate, a benzenesulfonate, and a toluenesulfonate) and a carboxylate (e.g., an acetate, a citrate, a maleate, a fumarate, a lactate, and an oxalate). These acid addition salts may also be present as a hydrate thereof.

Step 11:

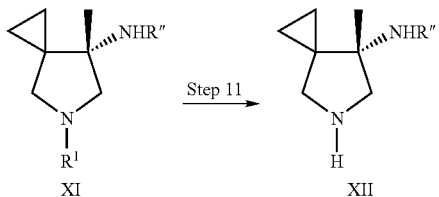

(wherein $R^1$ and R" have the same meanings as defined above)

In Step 11, the 5-position amino group ($R^1$) of compound (XI) is deprotected, to thereby produce compound (XII).

The deprotection in Step 11 may be performed under the conditions appropriately selected in accordance with properties of protective group R". In this case, when the 7-position amino group is protected by R", only R' may be selectively removed. Although both $R^1$ and R" may be removed, removal of $R^1$ alone is preferred. Specifically, when R' is a benzyl group, a benzhydryl group, a 1-(R)-phenylethyl group, or a 1-(S)-phenylethyl group, deprotection is generally performed using catalytic hydrogenolysis in a solvent which can dissolve compound (XI) such as methanol, ethanol or isopropanol, under hydrogen atmosphere at ambient pressure to under pressurized conditions, in the presence of a palladium-carbon catalyst. The reaction may be performed at room temperature to 50° C. Instead of hydrogen gas, a hydrogen donor such as ammonium formate may be used in an alcoholic solvent. Alternatively, Birch's reduction, which employs metallic sodium in liquid ammonia, may also be employed. When R¹ is a triphenylmethyl group, hydrochloric acid may also be used in acetone under the aforementioned deprotection conditions. In this case, a 7-positioned protective group for amino group must be stable under acidic conditions attained by hydrochloric acid.

The compound (XII):

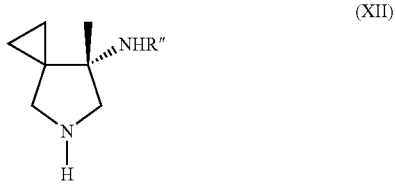

(XII)

(wherein R" has the same meaning as defined above) produced in Step 11 may be present as a free amine (dibasic form) or an acid addition salt thereof. Examples of the acid addition salt include inorganic salts and organic salts. Specific examples of the inorganic salts and the organic salts include inorganic acid salts such as a hydrochloride, a sulfate, a nitrate, a hydrobromide, a hydroiodide, and a phosphate; and organic acid salts such as a sulfonate (e.g., a mathanesulfonate, a benzenesulfonate, and a toluenesulfonate) and a carboxylate (e.g., an acetate, a citrate, a maleate, a fumarate, a lactate, and an oxalate). These acid addition salts may also be present as a hydrate thereof.

EXAMPLES

The present invention will hereinafter be described in detail by way of Examples, which should not be construed as limiting the invention thereto.

Referential Example 1 tert-Butyl 5-oxo-1-[(1R)-1-phenylethyl]pyrrolidine-3-carboxylate

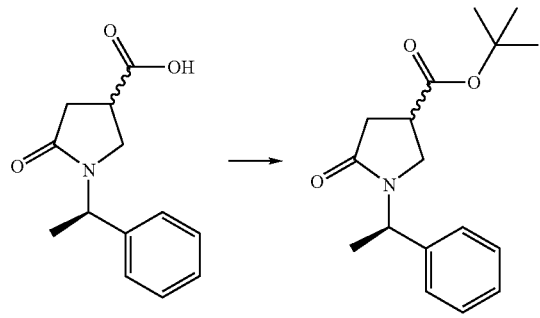

Under stirring by means of an impeller, O-tert-butyl-N,N'-diisopropylurea (3,020 g, 15.00 mol) was added at room temperature to a suspension of 5-oxo-1-[(1R)-1-phenylethyl]pyrrolidine-3-carboxylic acid (1,165 g, 4.994 mol) in dichloromethane (10 L). After rising in internal temperature and initiation of reflux had been observed, the mixture was cooled in an ice-water bath. The reaction mixture was cooled to room temperature. Thereafter, the ice-water bath was removed, and the reaction mixture was stirred for 1 hour, and subsequently, for 3 hours under heating at 40° C. The reaction mixture was further stirred for 1 hour with cooling in an ice-water bath, and insoluble material was removed through filtration. The filtrate was evaporated to dryness under reduced pressure, and the residue was purified through silica gel column chromatography (silica gel: 4 kg, eluent; hexane:ethyl acetate=3:1), to thereby yield the title compound as pale yellow syrup (3-position isomer mixtures) (925.2 g, 64%). The diastereomers in terms of the 3-position of pyrrolidine can be easily separable. However, since the subsequent step include reaction involving epimerization, the diastereomers were used without performing purification. ¹H-NMR spectral data of each diastereomer, which had been separately isolated, are given below.

Low-Polar Isomer:
¹H-NMR (400 MHz, CDCl₃) δ: 1.45 (9H, s), 1.54 (3H, d, J=7.08 Hz), 2.59-2.74 (2H, m), 2.95-3.03 (1H, m), 3.14 (1H, dd, J=9.77, 8.79 Hz), 3.49 (1H, dd, J=9.77, 6.35 Hz), 5.50 (1H, q, J=7.1 Hz), 7.26-7.36 (5H, m).

High-Polar Isomer:
¹H-NMR (400 MHz, CDCl₃) δ: 1.36 (9H, s), 1.53 (3H, d, J=7.32 Hz), 2.59-2.75 (2H, m), 3.02-3.11 (1H, m), 3.16 (1H, dd, J=10.01, 5.62 Hz), 3.51 (1H, dd, J=10.01, 8.54 Hz), 5.50 (1H, q, J=7.1 Hz), 7.24-7.36 (5H, m)

Referential Example 2 tert-Butyl 5-oxo-1-[(1R)-1-phenylethyl]pyrrolidine-3-carboxylate (alternative synthesis method)

Oxalyl chloride (224 µL, 2.57 mmol) and N,N-dimethylformamide (1 drop) were added under ice-cooling to a solution of 5-oxo-1-[(R)-1-phenylethyl]pyrrolidine-3-carboxylic acid (500 mg, 2.14 mmol) in dichloromethane (2.67 mL). The mixture was stirred under ice-cooling for 15 minutes, and then stirred at room temperature for 15 minutes. Toluene was added to the resultant mixture and then the solvent was evaporated to dryness under reduced pressure. This procedure (addition of toluene and solvent evaporation) was repeated twice to yield vermilion oil (603 mg). A solution of tert-butanol (614 µL, 6.42 mmol) in dichloromethane (2.67 mL) was prepared in a separate vessel, and a solution of the aforementioned vermilion oil (603 mg) dissolved in dichloromethane (2.67 mL) was added dropwise to the tert-butanol solution under a nitrogen atmosphere under ice-cooling. Triethylamine (448 µL, 3.21 mmol) was added to the reaction mixture, followed by stirring at room temperature for 30 minutes. Subsequently, water (10 mL) was added to the mixture, followed by extraction with dichloromethane (10 mL×2). The thus-obtained organic layer was washed with saturated brine (25 mL) and dried over sodium sulfate anhydrate. After filtration, the filtrate was concentrated under reduced pressure. Toluene was added to the concentration residue, followed by evaporating to dryness under reduced pressure. This procedure (addition of toluene and solvent evaporation) was repeated twice. The residue (558 mg) was purified through short silica gel column chromatography (eluent: 100% ethyl acetate), to thereby yield a pale yellow product (523 mg, 85%) of the title compound as a diastereomer mixture (diastereomer ratio=2.2:1.0).

¹H-NMR (400 MHz, CDCl₃) δ: 1.36 (2.81/9H, s), 1.45 (6.19/9H, s) 1.53 (0.93/3Hd, J=3.7 Hz), 1.54 (2.06/3H, d,

J=3.7 Hz), 2.59-2.75 (2H, m), 2.95-3.18 (2H, m), 3.47-3.53 (1H, m), 5.50 (1H, q, J=7.1 Hz), 7.25-7.37 (5H, m).

Example 1 tert-Butyl (3S)-3-methyl-5-oxo-1-[(1R)-1-phenylethyl]pyrrolidine-3-carboxylate

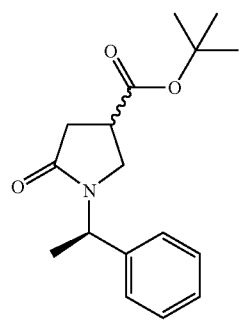

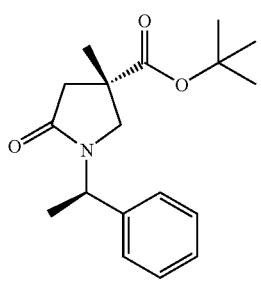

Under a nitrogen gas atmosphere, iodomethane (26.0 mL, 59.28 g, 0.418 mol) and sodium hydride (55% in oil, 11.35 g, 0.260 mol) were sequentially added at room temperature to a solution of tert-butyl 5-oxo-1-[(1R)-1-phenylethyl]pyrrolidine-3-carboxylate (30.05 g, 0.104 mol) in N,N'-dimethylformamide (210 mL) under stirring. When the internal temperature reached to about 50° C., the mixture was cooled to 30° C. in an ice-water bath. Subsequently, the bath was changed to a water bath having an external temperature of 17° C., followed by stirring for 23 hours. The reaction mixture was poured into cold aqueous citric acid (a mixture of 10% citric acid (1 L) and ice (500 g)), followed by stirring for 30 minutes and extracting with ethyl acetate mL, 500 mL). The organic layers were combined and washed with saturated brine, followed by drying over sodium sulfate anhydrate and filtration. The filtrate was evaporated to dryness under reduced pressure. The residue was purified through flash silica gel column chromatography (eluent; hexane:ethyl acetate=5:1 to 4:1), to thereby yield the title compound as white solid (10.63 g, 33.7%) as a high-polar isomer. In addition, tert-butyl (3R)-3-methyl-5-oxo-1-[(1R)-1-phenylethyl]pyrrolidine-3-carboxylate (14.91 g, 47.3%) was produced as a low-polar isomer.

$^1$H-NMR (400 MHz, CDCl$_3$) δ: 1.34 (12H, s), 1.52 (3H, d, J=7.0 Hz), 2.27 (1H, d, J=17.0 Hz), 2.93 (1H, d, J=17.0 Hz), 3.05 (1H, d, J=10.1 Hz), 3.32 (1H, d, J=10.1 Hz), 5.50 (1H, q, J=7.1 Hz), 7.23-7.38 (5H, m).

Example 2 tert-Butyl (3S)-4-[2-(tert-butyldimethylsilyl)hydroxyethyl]-3-methyl-5-oxo-1-[(1R)-phenylethyl]pyrrolidine-3-carboxylate

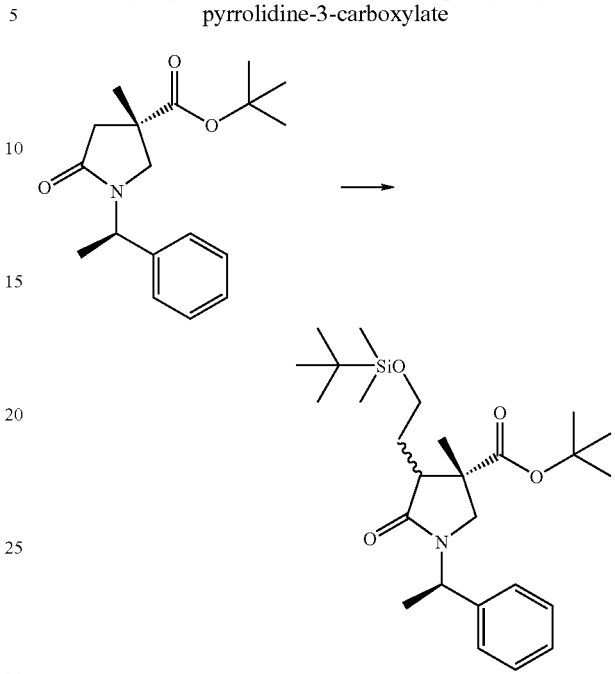

tert-Butyl (3S)-3-methyl-5-oxo-1-[(1R)-phenylethyl]pyrrolidine-3-carboxylate (30.0 g, 98.9 mmol) and tert-butyl (2-iodoethoxy)dimethylsilane (36.8 g, 129 mmol) were dissolved in anhydrous tetrahydrofuran (288 mL), and lithium bis(trimethylsilyl)amide (1.0M tetrahydrofuran solution, 129 mL, 129 mmol) was added dropwise to the solution at −4° C., followed by stirring at 2° C. for 3.5 hours. Subsequently, saturated aqueous ammonium chloride solution (300 mL) was added to the reaction mixture, followed by extraction with ethyl acetate (300 mL, 200 mL). The thus-obtained organic layer was washed with saturated brine (200 mL), followed by drying over sodium sulfate anhydrate and filtration. The filtrate was evaporated to dryness under reduced pressure, to thereby yield the title compound (54.1 g). The thus-obtained compound was used in the subsequent step without any purification.

M(ESI) m/z: 363 (M-Boc+H)$^+$.

Example 3 tert-Butyl (3S)-4-(2-hydroxyethyl)-3-methyl-5-oxo-1-[(1R)-phenylethyl]pyrrolidine-3-carboxylate

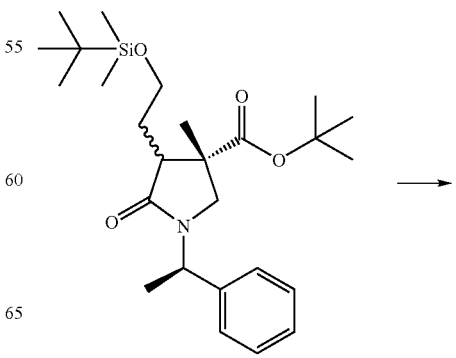

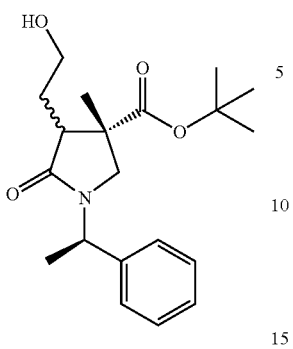

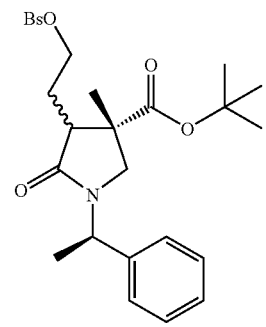

The aforementioned crude silyl compound (54.1 g, 98.9 mmol) was dissolved in tetrahydrofuran (450 mL). A 1.0 mol/L solution of tetrabutylammonium fluoride (148 mmol) in tetrahydrofuran solution (148 mL) was added dropwise to the solution under ice-cooling, and the mixture was stirred at room temperature for 2 hours. The reaction mixture was concentrated, followed by extraction with ethyl acetate (200 mL, 100 mL). The thus-obtained organic layer was washed sequentially with 10% aqueous sodium hydrogencarbonate (200 mL), aqueous citric acid (300 mL), and saturated brine (100 mL), followed by drying over sodium sulfate anhydrate and filtration. The filtrate was evaporated to dryness under reduced pressure. The residue was purified through silica gel column chromatography (eluent; hexane:ethyl acetate=6:1 to 4:1 to 1:1), to thereby yield the title compound as colorless transparent syrup (29.1 g, 83.9 mmol, 85%).

$^1$H-NMR (400 MHz, CDCl$_3$) δ: 1.28 (3H, s), 1.40 (9H, s), 1.51-1.53 (1H, m), 1.53 (3H, d, J=7.1 Hz), 1.78-1.94 (2H, m), 2.90-3.08 (2H, m), 3.67-3.75 (1H, m), 3.80-3.91 (1H, m), 4.85-4.89 (1H, m), 5.43-5.53 (1H, m), 7.27-7.37 (5H, m).

M(ESI) m/z: 348 (M+H)$^+$.

Triethylamine (15.2 mL, 109 mmol), benzenesulfonyl chloride (11.8 mL, 92.3 mmol), and 4-dimethylaminopyridine (1.02 g, 8.39 mmol) were added to a solution of tert-butyl (3S)-4-(2-hydroxyethyl)-3-methyl-5-oxo-1-[(1R)-phenylethyl]pyrrolidine-3-carboxylate (29.1 g, 83.9 mmol) in dichloromethane (280 mL) under ice-cooling, and the mixture was stirred at room temperature for 19 hours. Subsequently, saturated aqueous ammonium chloride (280 mL) was added to the reaction mixture. The organic layer was separated, and the solvent thereof was evaporated under reduced pressure. The residue was dissolved in ethyl acetate (280 mL, 180 mL), and the solution was washed again with the same saturated aqueous ammonium chloride as employed above. The organic layer was washed sequentially with 1 mol/L aqueous hydrochloric acid (250 mL), saturated aqueous sodium bicarbonate (250 mL), and saturated brine (200 mL), followed by drying over sodium sulfate anhydrate and filtration. The filtrate was evaporated to dryness under reduced pressure, to thereby yield a crude product of the title benzenesulfonyl compound (43.7 g). The thus-obtained compound was used in the subsequent step without performing purification.

M(ESI) m/z: 510 (M+Na)$^+$.

Example 4 tert-Butyl (3S)-4-[2-(benzenesulfonyl)oxyethyl]-3-methyl-5-oxo-1-[(1R)-phenylethyl]pyrrolidine-3-carboxylate Example 5 tert-Butyl (7S)-7-methyl-4-oxo-5-[(1R)-phenylethyl]-5-azaspiro[2.4]heptane-7-carboxylate

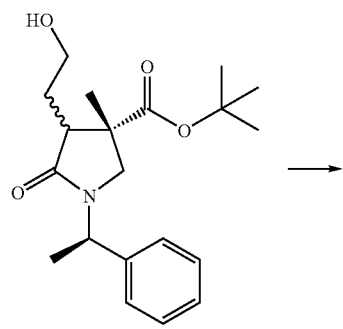

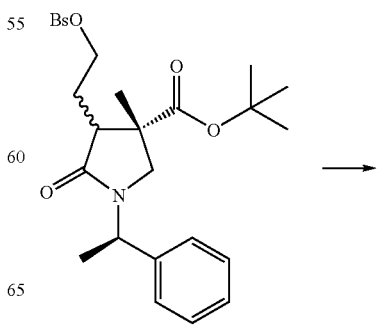

-continued

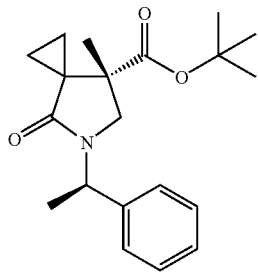

A 1.0 mol/L solution of sodium bis(trimethylsilyl)amide in tetrahydrofuran (109 mL, 109 mmol) was added under ice-cooling to a solution of the crude benzenesulfonyl compound (43.7 g, 83.9 mmol), which had been produced in the precedent step, in anhydrous tetrahydrofuran (470 mL). The mixture was stirred at room temperature for 1 hour. Subsequently, saturated aqueous ammonium chloride (300 mL) was added to the reaction mixture, followed by extraction with ethyl acetate (300 mL, 200 mL). The organic layer was washed with saturated brine (200 mL). The organic layer was dried over sodium sulfate anhydrate, followed by filtration. The filtrate was evaporated to dryness under reduced pressure. The residue was purified through silica gel column chromatography (eluent; hexane:ethyl acetate=3:1 to 2:1), to thereby yield the title compound as white solid (24.6 g, 89%, 2 steps).

mp: 55-57° C.

$[\alpha]_D^{25.1}=122.1°$ (c=0.517, CHCl$_3$).

$^1$H-NMR (400 MHz, CDCl$_3$) δ: 0.72-0.77 (1H, m), 0.85-0.90 (1H, m) 1.04-1.13 (2H, m), 1.18 (3H, s), 1.32 (9H, s), 1.54 (3H, d, J=7.1 Hz), 3.08 (1H, d, J=9.8 Hz), 3.53 (1H, d, J=9.8 Hz), 5.52 (1H, q, J=7.1 Hz), 7.26-7.34 (5H, m).

Elemental analysis: as $C_{20}H_{27}NO_3$: Calculated: C, 72.92; H, 8.26; N, 4.25. Found: C, 72.64; H, 8.27; N, 4.06.

MS (FAB) m/z: 330 (M+H)$^+$.

HRMS (FAB) m/z: 330.2069 (Calcd for $C_{20}H_{28}NO_3$ 330.2069).

IR (ATR)ν: 3066, 2976, 2933, 2879, 1720, 1676, 1481, 1454, 1433, 1365, 1329, 1286, 1238, 1203 cm$^{-1}$.

Configuration of the 7-position of the compound was determined through X-ray structural analysis. The results are shown below in detail.

TABLE 1

| | |
|---|---|
| Crystal size | 0.40 mm × 0.30 mm × 0.34 mm |
| Radiation | CuKα(1.54178 Å) |
| Tube current | 50 kV |
| Tube Voltage | 80 mA |
| Diffractometer | AFC7R |
| Temperature | 24° C. |
| Formula | C20H27NO3 |
| Formula weight | 329.44 |
| Crystal system | orthorhombic |
| Space group | P2$_1$2$_1$2$_1$ |
| Z value | 4 |
| Cell parameters | a = 16.3960(19) Å    b = 17.1223(20) Å    c = 6.7995(14) Å |
| | α = 90.000( )°    β = 90.000( )°    γ = 90.000( )° |
| d$_{calc}$ | 1.14 g/cm$^3$ |
| No. of reflection measured | 1665 (unique) |
| μ | 6.09 cm$^{-1}$ |
| Phase determination | Direct method (Software: SIR92) |
| Phase refinement | Full matrix least-square |
| R1 | 5.9% = Σ||Fo| − |Fc||/Σ|Fo| for I > 2.0σ data |
| R | 6.3% = Σ(Fo$^2$ − Fc$^2$)/ΣFo$^2$ |
| Rw | 19.1% = [Σw(Fo$^2$ − Fc$^2$)$^2$/Σw(Fo$^2$)$^2$]$^{1/2}$ where |

After collection of the data, initial phase was determined through the direct method and refined by the complete matrix least square method. In the refining, an anisotropic thermal factor was applied to non-hydrogen atoms, and the positions of hydrogen atoms were fixed in the coordinates through calculation. The compound contains two asymmetric carbon atoms, and absolute configuration of one asymmetric carbon atom is already known. According to this absolute configuration, absolute configuration of the other asymmetric carbon atom was determined. FIG. 1 shows the results. As shown in FIG. 1, the configuration of the 7-position of the title compound was determined as (S). Thus, configuration of a series of compounds prepared from the compound could also be determined.

Example 6 tert-Butyl (3S)-4-(2-iodoethyl)-3-methyl-5-oxo-1-[(1R)-phenylethyl]pyrrolidine-3-carboxylate

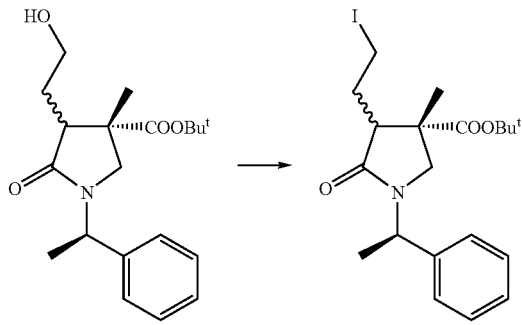

Triethylamine (0.22 mL, 1.6 mmol) and methanesulfonyl chloride (99 µL, 1.28 mmol) were added under ice-cooling to a solution of tert-butyl (3S)-4-(2-hydroxyethyl)-3-methyl-5-oxo-1-[(1R)-phenylethyl]pyrrolidine-3-carboxylate (0.37 g, 1.07 mmol) in dichloromethane (7.5 mL), and the mixture was stirred at room temperature for 2.5 hours. Subsequently, water (20 mL) was added to the reaction mixture, followed by extraction with chloroform (20 mL×3). The extract was washed with saturated brine (20 mL), followed by drying over sodium sulfate anhydrate and filtration. The filtrate was evaporated to dryness under reduced pressure. The residue was dissolved in acetone (20 mL). Sodium iodide (0.32 g, 2.13 mmol) was added to the solution, followed by stirring at 80° C. for 17.5 hours. The reaction mixture was concentrated under reduced pressure. Water (20 mL) was added to the residue, followed by extraction with ethyl acetate (20 mL×3). The extract was washed sequentially with 10% aqueous sodium thiosulfate (20 mL) and saturated brine (20 mL). The organic layer was dried over sodium sulfate anhydrate and filtered. The filtrate was evaporated to dryness under reduced pressure, to thereby yield the title compound as pale yellow oil (0.47 g, 96%).

¹H-NMR (400 MHz, CDCl₃) δ: 1.20 (3H, s), 1.43 (9H, s) 1.50 (3H, d, J=7.1 Hz), 2.00-2.10 (1H, m), 2.16-2.27 (1H, m), 2.85 (1H, dd, J=9.0, 4.9 Hz), 2.93 (1H, d, J=10.0 Hz), 3.24 (1H, d, J=10.0 Hz), 3.55 (2H, dd, J=8.1, 6.3 Hz), 5.48 (1H, q, J=7.1 Hz), 7.25-7.37 (5H, m).

M(ESI) m/z: 458 (M+H)⁺.

Example 7 tert-Butyl (7S)-7-methyl-4-oxo-5-[(1R)-phenylethyl]-5-azaspiro[2.4]heptane-7-carboxylate

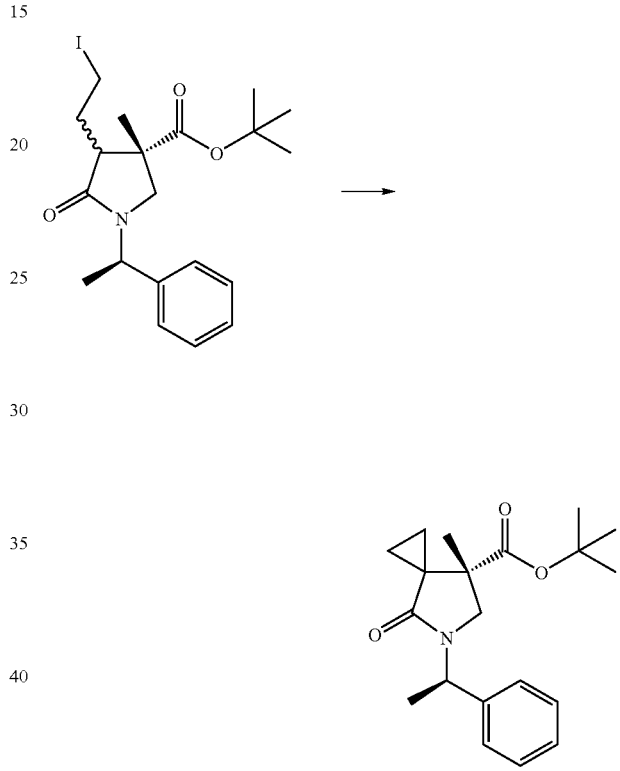

Potassium bis(trimethylsilyl)amide (0.5M toluene solution, 0.62 mL, 0.31 mmol) was added under ice-cooling to a solution of tert-butyl (3S)-4-(2-iodoethyl)-3-methyl-5-oxo-1-[(1R)-phenylethyl]pyrrolidine-3-carboxylate (118 mg, 0.26 mmol) in anhydrous tetrahydrofuran (2.4 mL), the mixture was stirred under ice-cooling for 10 minutes. Subsequently, saturated aqueous ammonium chloride (20 mL) was added to the reaction mixture, followed by extraction with ethyl acetate mL×3). The extract was washed sequentially with 10% aqueous sodium thiosulfate (20 mL) and saturated brine (20 mL). The organic layer was dried over sodium sulfate anhydrate, and the solvent was evaporated under reduced pressure. The residue was purified through silica gel column chromatography (hexane:ethyl acetate=4:1), to thereby yield the title compound as a colorless solid (91 mg, 100%).

¹H-NMR data of this product were found to coincide with those obtained in Example 5.

M(ESI) m/z: 330 (M+H)⁺.

Example 8 tert-Butyl (3S)-3-methyl-4-methylene-5-oxo-1-[(1R)-1-phenylethyl]pyrrolidine-3-carboxylate

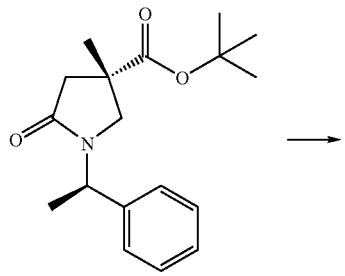

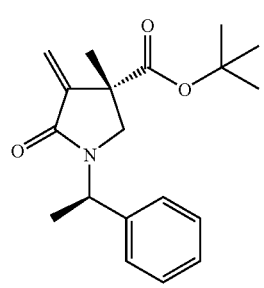

tert-Butyl (3S)-3-methyl-5-oxo-1-[(1R)-1-phenylethyl]pyrrolidine-3-carboxylate (200 mg, 0.66 mmol) was dissolved in anhydrous tetrahydrofuran (4 mL). A 1.0M solution (1.45 mL, 1.45 mmol) of lithium hexamethyldisilazide in tetrahydrofuran was added to the solution at 0° C., followed by stirring for 30 minutes at the same temperature.

Subsequently, ethyl formate (69 µL, 0.86 mmol) was added to the mixture at 0° C., followed by stirring at the same temperature for 1 hour and 20 minutes. Thereafter, N,N-dimethylformamide (4 mL) and paraformaldehyde (120 mg) were added to the stirred mixture, followed by stirring at room temperature for 17 hours. 1M Aqueous hydrochloric acid was added at 0° C. to the reaction mixture for termination of reaction, followed by extraction with ethyl acetate three times. The combined organic layer was washed with saturated brine, and dried over sodium sulfate anhydrate. After filtration, the filtrate was concentrated under reduced pressure. The residue was purified through medium pressure liquid chromatography (eluent; hexane:ethyl acetate=1:1), to thereby yield the title compound as a colorless solid (127 mg, 61%).

$^1$H-NMR (400 MHz, CDCl$_3$) δ: 1.30 (9H, s), 1.43 (3H, s) 1.57 (3H, d, J=7.1 Hz), 3.03 (1H, d, J=10.0 Hz), 3.56 (1H, d, J=10.0 Hz), 5.50 (1H, s), 5.63 (1H, q, J=7.1 Hz), 6.12 (1H, s), 7.24-7.35 (5H, m).

IR (ATR)v: 1724, 1687, 1427, 1369, 1315, 1279, 1230, 1161, 1132, 700 cm$^{-1}$.

MS (ESI) m/z: 316 (M+1)$^+$.

HRMS(EI) m/z: 315.1842 (Calcd for C$_{19}$H$_{25}$NO$_3$ 315.1834).

Example 9 tert-Butyl (7S)-7-methyl-4-oxo-5-[(1R)-1-phenylethyl]-5-azaspiro[2.4]heptane-7-carboxylate

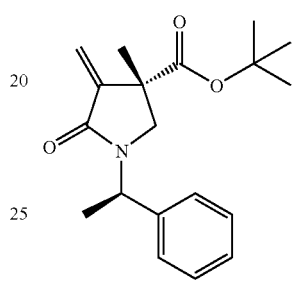

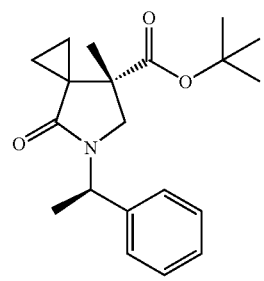

Sodium hydride (60% in oil, 76.1 mg, 1.74 mmol) and a solution of tert-butyl (3S)-3-methyl-4-methylene-5-oxo-1-[(1R)-1-phenylethyl]pyrrolidine-3-carboxylate (500 mg, 1.59 mmol) in dimethylsulfoxide (24 mL) were added sequentially to a solution of trimethylsulfonium iodide (401 mg, 1.82 mmol) in dimethylsulfoxide (8 mL), and the mixture was stirred at 90° C. for 30 minutes. 10% Aqueous citric acid (32 mL) and water (96 mL) were added to the reaction mixture at room temperature, followed by extraction with ethyl acetate (200 mL×2). The obtained organic layer was washed sequentially with water (100 mL) and saturated brine (100 mL). The organic layer was dried over sodium sulfate anhydrate. After filtration, the filtrate was evaporated to dryness under reduced pressure. The residue was purified through silica gel column chromatography (eluent; hexane:ethyl acetate 3:1 to 2:1), to thereby yield the title compound as colorless crystals (315 mg, 60.3%). $^1$H-NMR and IR spectral data of this product were found to coincide with those obtained in Example 5.

MS (FAB+) m/z: 330 (M+H)$^+$.

HRMS (FAB+) m/z: 330.2069 (Calcd for C$_{20}$H$_{28}$NO$_3$ 330.2069).

Example 10

(7S)-7-Methyl-4-oxo-5-[(1R)-phenylethyl]-5-azaspiro[2.4]heptane-7-carboxylic acid

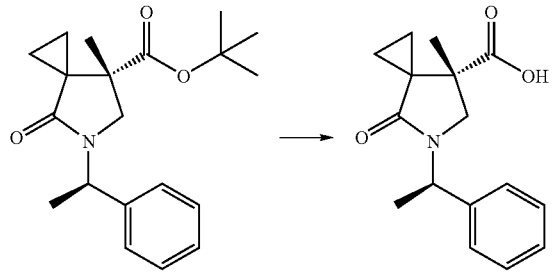

Trifluoroacetic acid (120 mL) was added dropwise to a solution of tert-butyl (7S)-7-methyl-4-oxo-5-[(1R)-phenylethyl]-5-azaspiro[2.4]heptane-7-carboxylate (24.5 g, 74.4 mmol) in dichloromethane (120 mL) under ice-cooling, followed by stirring for 2 hours. The reaction mixture was evaporated to dryness under reduced pressure. Toluene (20 mL) was added to the residue, and the mixture was evaporated to dryness under reduced pressure. The residue was dissolved in 1-mol/L aqueous sodium hydroxide (300 mL) under ice-cooling. The resultant aqueous solution was washed with ethyl acetate (350 mL). Concentrated hydrochloric acid (25 mL) was added under ice-cooling to the aqueous layer so as to adjust the pH of the layer to 2 to 3, followed by extraction with chloroform (300 mL×2). The organic layer was washed sequentially with water (200 mL) and saturated brine (100 mL). The washed layer was dried over sodium sulfate anhydrate, and the solvent was evaporated under reduced pressure. Toluene (20 mL) was added to the residue, and the mixture was evaporated to dryness under reduced pressure. The residue was suspended in chloroform (20 mL), and hexane (200 mL) was added to the suspension for crystallization. The precipitated solid was washed with hexane (100 mL) and dried under reduced pressure, to thereby yield the title compound as white solid (20.48 g (quantitative)). The thus-obtained compound was used in the subsequent step without performing purification.

$^1$H-NMR (400 MHz, CDCl$_3$) δ: 0.78-0.83 (1H, m), 0.90-0.95 (1H, m), 1.08-1.18 (2H, m), 1.24 (3H, s), 1.55 (3H, d, J=7.3 Hz), 3.11 (1H, d, J=10.0 Hz), 3.55 (1H, d, J=10.0 Hz), 5.52 (1H, q, J=7.1 Hz), 7.28-7.32 (5H, m).

MS (ESI) m/z: 274 (M+H)$^+$.

Example 11

(7S)-7-Amino-7-methyl-4-oxo-5-[(1R)-phenylethyl]-5-azaspiro[2.4]heptane

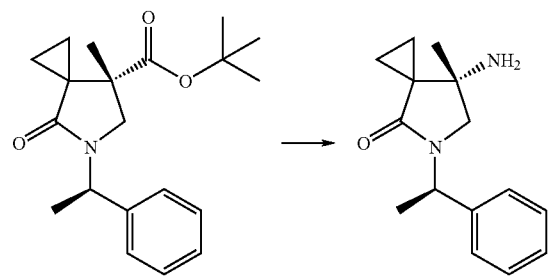

(7S)-7-Methyl-4-oxo-5-[(1R)-phenylethyl]-5-azaspiro[2.4]heptane-7-carboxylic acid (20.4 g, 74.4 mmol) and diphenylphosphoryl azide (17.6 mL, 81.8 mmol) were dissolved in toluene (200 mL), and triethylamine (20.7 mL, 149 mmol) was added to the solution, followed by stirring under heating in an oil bath (at 125° C.) for 1 hour. The reaction mixture was concentrated under reduced pressure, to thereby yield a crude isocyanate compound.

The crude isocyanate compound was dissolved in 1,4-dioxane (180 mL), and water (90 mL) and concentrated hydrochloric acid (90 mL) were added to the solution, followed by stirring under heating in an oil bath (at 50° C.) for 1 hour. Subsequently, water (200 mL) was added to the reaction mixture, and the mixture was washed with ethyl acetate (200 mL). 10 mol/L Aqueous sodium hydroxide (170 mL) was added under ice-cooling to the aqueous layer so as to adjust the pH of the layer to 9 to 10, followed by extraction with toluene (200 mL×2). The organic layer was washed with saturated brine (100 mL), dried over sodium sulfate anhydrate, and filtered. The filtrate was concentrated under reduced pressure, to thereby yield the title compound as pale yellow oil (15.8 g, 64.7 mmol). The thus-obtained compound was used in the subsequent step without any purification.

$^1$H-NMR (400 MHz, CDCl$_3$) δ: 0.72-0.78 (2H, m), 0.99-1.10 (2H, m), 1.08 (3H, s), 1.53 (3H, d, J=7.4 Hz), 2.82 (1H, d, J=9.6 Hz), 3.27 (1H, d, J=9.6 Hz), 5.56 (1H, q, J=7.1 Hz), 7.14-7.37 (5H, m).

Example 12

(7S)-7-(tert-Butoxycarbonylamino)-7-methyl-5-[(1R)-phenylethyl]-5-azaspiro[2.4]heptane

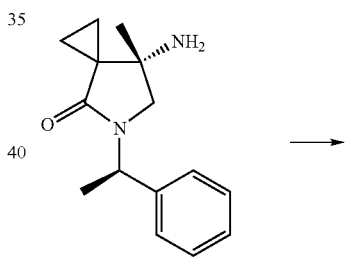

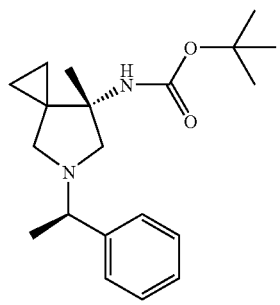

The aforementioned (7S)-7-Amino-7-methyl-4-oxo-5-[(1R)-phenylethyl]-5-azaspiro[2.4]heptane (15.8 g, 64.7 mmol) was dissolved in toluene (82 mL). Separately, 65 wt. % sodium bis(2-methoxyethoxy) aluminum hydride (259 mmol) in toluene mL) was prepared, and an aliquot (6 mL) of the solution was added dropwise to the azaspiroheptane solution over 15 minutes. Through ice-cooling, the internal temperature of the reaction mixture was controlled so as not to exceed 70° C. The resultant mixture was stirred under heating in an oil bath (at 80° C.) for 10 minutes. The reaction mixture was ice-cooled, and 25 wt. % aqueous sodium hydroxide (158 mL) was added dropwise thereto for termination of reaction, followed by extraction with toluene (135 mL). The organic layer was washed with saturated brine (100 mL), and di-tert-butyl dicarbonate (15.6 g, 71.2 mmol) was added to the washed layer. The reaction mixture was stirred at room temperature for 3 hours, and the solvent was evaporated under reduced pressure. The residue was purified through silica gel column chromatography (eluent; hexane:ethyl acetate=8:1 to 4:1 to 1:1), to thereby yield the title compound as colorless transparent syrup (18.0 g, 73%).

$^1$H-NMR (400 MHz, CDCl$_3$) δ: 0.37-0.49 (2H, m), 0.62-0.68 (1H, m) 0.77-0.82 (1H, m), 1.20 (3H, s), 1.32 (3H, d, J=6.6 Hz), 1.44 (9H, s), 2.46 (2H, dd, J=33.2, 9.3 Hz), 2.68 (1H, d, J=8.8 Hz), 3.27 (1H, q, J=6.6 Hz), 3.31-3.34 (1H, m), 4.71 (1H, s), 7.19-7.34 (5H, m).

MS (ESI) m/z: 331 (M+H)$^+$.

Example 13

(7S)-7-(tert-Butoxycarbonylamino)-7-methyl-5-azaspiro[2.4]heptane

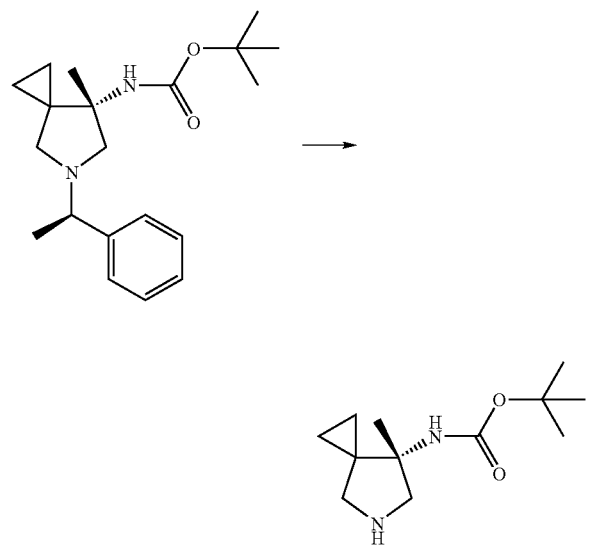

10% Palladium carbon (water content: 52.8%, 9.00 g) serving as a catalyst was added to a solution of (7S)-7-(tert-butoxycarbonylamino)-7-methyl-5-[(1R)-phenylethyl]-5-azaspiro[2.4]heptane (18.0 g, 54.5 mmol) in methanol (180 mL), and the mixture was stirred at room temperature under a hydrogen gas atmosphere for 18 hours. The mixture was further stirred in an oil bath (at 40° C.) for 5.5 hours. The catalyst was removed through filtration, and the solvent was evaporated to dryness under reduced pressure, to thereby yield a crude product of the title compound as white solid g (quantitative)).

$^1$H-NMR (400 MHz, CDCl$_3$) δ: 0.38-0.43 (1H, m), 0.54-0.61 (2H, m), 0.74-0.80 (1H, m), 1.08 (3H, s), 1.44 (9H, s), 2.75 (1H, d, J=7.6 Hz), 2.78 (1H, d, J=7.1 Hz), 3.13 (1H, d, J=11.5 Hz), 3.73-3.77 (1H, m), 4.45 (1H, s).

MS (ESI) m/z: 227 (M+H)$^+$.

Example 14

7-[(7S)-7-Amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid

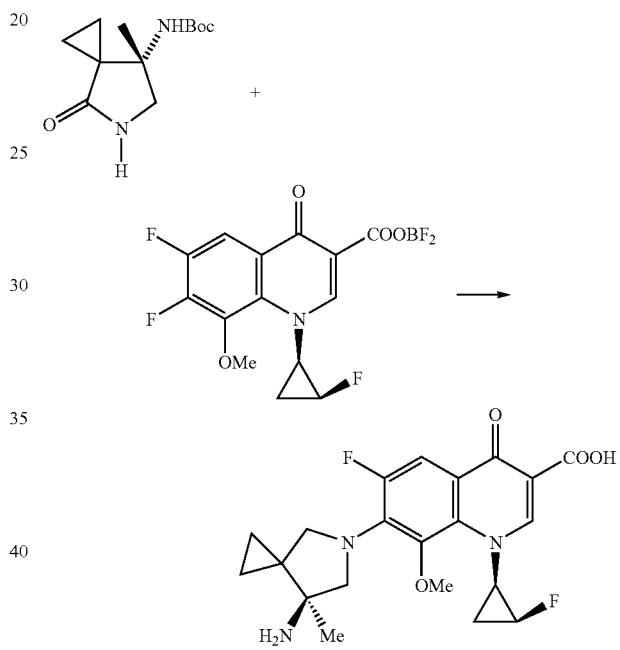

(7S)-7-(tert-Butoxycarbonylamino)-7-methyl-5-azaspiro[2.4]heptane (13.4 g, 54.5 mmol), 6,7-difluoro-1-[(1R,2S)-2-fluorocyclopropyl]-8-methoxy-1,4-dihydro-4-oxoquinoline-3-carboxylic acid-difluoroborane complex (17.9 g, 49.5 mmol), and triethylamine (8.97 mL, 64.4 mmol) were dissolved in dimethyl sulfoxide (52 mL), followed by stirring under heating in an oil bath (at 40° C.) for 17 hours. The reaction mixture was poured into cold water (1,000 mL), and the precipitated solid was recovered through filtration. Triethylamine (15 mL) and a mixture (180 mL) of ethanol and water (5:1) were added to the solid, followed by refluxing for 1.5 hours. The reaction mixture was evaporated to dryness under reduced pressure. The residue was dissolved in ethyl acetate (150 mL×2), followed by washing sequentially with 10% aqueous citric acid (200 mL), water (200 mL), and saturated brine (100 mL). The organic layer was dried over sodium sulfate anhydrate, and the solvent was evaporated under reduced pressure. The residue was dissolved in a mixture (100 mL) of chloroform and methanol (9:1), and silica gel (10 g) was added to the solution, followed by stirring for 1 hour. Thereafter, silica gel was removed from the mixture through filtration, and the silica gel was washed with a mixture of chloroform and methanol (9:1) (50 mL×2). The filtrate and wash liquid were combined, followed by concentration to dryness. The residue was dissolved in concentrated hydrochloric acid (200 mL) under ice-cooling, and the solution was stirred at room temperature for 30 minutes. The reaction mixture was washed with chloroform (400 mL×5). 10 mol/L Aqueous sodium hydroxide was added under ice-cooling to the aqueous layer so as to adjust the pH of the layer to 11.8. Subsequently, the pH of the layer was adjusted to 7.4 with hydrochloric acid, followed by extraction with chloroform (1,000 mL×3). The organic layer was dried over sodium sulfate anhydrate, and the solvent was evaporated under reduced pressure. The residue was recrystallized from ethanol for purification and dried under reduced pressure, to thereby yield the title compound as pale pink powder (18.5 g, 79%).

Analytical data of the resultant product obtained by means of apparatuses including $^1$H-NMR completely identical to those of the compound of Example 9 described in Japanese Patent Application No. 2005-146386. Thus, among 7-amino-7-methyl-5-azaspiro[2.4]heptan-5-yl group-containing quinolone derivatives disclosed in Japanese Patent Application No. 2005-146386, the 7-position configuration the quinolone derivative, which is a highly active compound described in Example 9, was determined as (7S).

The invention claimed is:

1. A method for producing a compound represented by formula (VII):

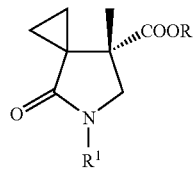

(VII)

wherein R represents an aryl group which may have a substituent, an aralkyl group which may have a substituent, a C1 to C6 alkyl group which may have a substituent, or a chiral auxiliary which can form an ester bond with carboxylic acid; and $R^1$ represents an aralkyl group which may have a substituent, which comprises:

reacting a compound represented by formula (I):

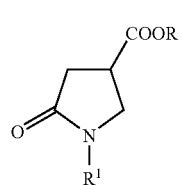

(I)

wherein R and $R^1$ have the same meanings as defined above, with a methylating reagent in the presence of a base to produce a compound represented by formula (II):

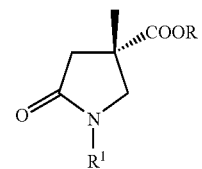

(II)

wherein $R^1$ and R have the same meanings as defined above;

reacting the compound represented by formula (II) with a compound represented by formula (III):

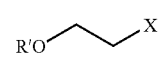

(III)

wherein R' represents a protective group for hydroxy group, and X represents a halogen atom or a leaving group employed in nucleophilic substitution, in the presence of a base to produce a compound represented by formula (IV):

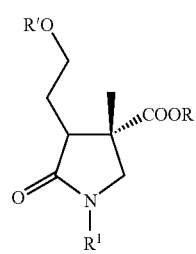

(IV)

wherein $R^1$, R, and R' have the same meanings as defined above;

removing the protective group for hydroxy group from the compound represented by formula (IV) to produce a compound represented by formula (V):

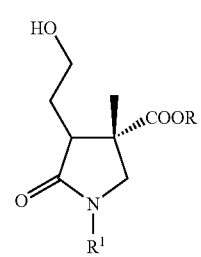

(V)

wherein $R^1$ and R have the same meanings as defined above;

transforming the hydroxy group of the compound represented by formula (V) to a halogen atom or a leaving group employed in nucleophilic substitution to form a compound represented by formula (VI):

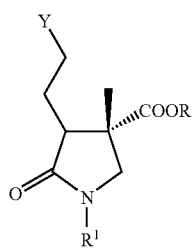

(V1)

wherein Y represents a halogen atom or a leaving group employed in nucleophilic substitution, and R¹ and R have the same meanings as defined above; and
treating the compound represented by formula (VI) under basic conditions.

2. The method according to claim 1, wherein R¹ is a 1-(R)-phenylethyl group or a 1-(S)-phenylethyl group.

3. The method according to claim 1, wherein R is a C1 to C6 alkyl group.

4. The method according to claim 1, wherein R is a tert-butyl group.

5. The method according to claim 1, wherein Y is a substituted sulfonyloxy group or a halogen atom.

6. The method according to claim 1, wherein Y is a benzenesulfonyloxy group or an iodine atom.

7. The method according to claim 1, wherein the compound represented by formula (VII) is a (7S)-7-methyl-4-oxo-5-[(1R)-phenylethyl]-5-azaspiro[2.4]heptane-7-carboxylate ester.

8. The method according to claim 1, wherein the compound represented by formula (VII) is tert-butyl (7S)-7-methyl-4-oxo-5-[(1R)-phenylethyl]-5-azaspiro[2.4] heptane-7-carboxylate.

9. A method for producing a compound represented by formula (VII):

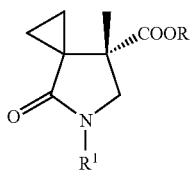

(VII)

wherein R represents an aryl group which may have a substituent, an aralkyl group which may have a substituent, a C1 to C6 alkyl group which may have a substituent, or a chiral auxiliary which can form an ester bond with carboxylic acid; and R¹ represents an aralkyl group which may have a substituent, which comprises:
exo-methylenating a compound represented by formula (II):

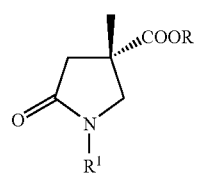

(II)

wherein R and R¹ have the same meanings as defined above, to produce a compound represented by formula (VIII):

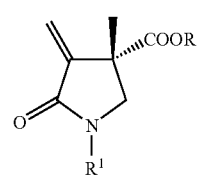

(VIII)

wherein R¹ and R have the same meanings as defined above; and
subjecting the exo-methylene group of the compound represented by formula (VIII) to a cyclopropanation.

10. The method according to claim 9, wherein R¹ is a 1-(R)-phenylethyl group or a 1-(S)-phenylethyl group.

11. The method according to claim 9, wherein R is a C1 to C6 alkyl group.

12. The method according to claim 9, wherein R is a tert-butyl group.

13. The method according to claim 9, wherein the compound represented by formula (VII) is a (7S)-7-methyl-4-oxo-5-[(1R)-phenylethyl]-5-azaspiro[2.4]heptane-7-carboxylate ester.

14. The method according to claim 9, wherein the compound represented by formula (VII) is tert-butyl (7S)-7-methyl-4-oxo-5-[(1R)-phenylethyl]-5-azaspiro[2.4]heptane-7-carboxylate.

* * * * *